US010723750B2

(12) United States Patent
Zajonc et al.

(10) Patent No.: US 10,723,750 B2
(45) Date of Patent: Jul. 28, 2020

(54) SPHINGAMIDE COMPOUNDS AND METHODS FOR BINDING INKT CELLS

(71) Applicants: La Jolla Institute for Allergy and Immunology, La Jolla, CA (US); Universiteit Gent, Ghent (BE); VIB VZW, Ghent (BE)

(72) Inventors: Dirk Zajonc, San Diego, CA (US); Serge Van Calenbergh, Ghent (BE); Dirk Elewaut, Ghent (BE); Joren Guillaume, Ghent (BE)

(73) Assignees: La Jolla Institute for Allergy and Immunology, La Jolla, CA (US); Universiteit Gent, Ghent (BE); VIB VZW, Ghent (BE)

( * ) Notice: Subject to any disclaimer, the term of this patent is extended or adjusted under 35 U.S.C. 154(b) by 0 days.

(21) Appl. No.: 15/775,770

(22) PCT Filed: Nov. 14, 2016

(86) PCT No.: PCT/US2016/061861
§ 371 (c)(1),
(2) Date: May 11, 2018

(87) PCT Pub. No.: WO2017/083830
PCT Pub. Date: May 18, 2017

(65) Prior Publication Data

US 2019/0256541 A1 Aug. 22, 2019

Related U.S. Application Data

(60) Provisional application No. 62/254,973, filed on Nov. 13, 2015.

(51) Int. Cl.

| | |
|---|---|
| *C07H 15/04* | (2006.01) |
| *A61K 47/65* | (2017.01) |
| *A61P 37/04* | (2006.01) |
| *A61P 31/12* | (2006.01) |
| *A61P 35/00* | (2006.01) |
| *A61K 31/7028* | (2006.01) |
| *A61K 31/739* | (2006.01) |
| *C07H 15/18* | (2006.01) |
| *C07H 15/06* | (2006.01) |

(52) U.S. Cl.
CPC ......... *C07H 15/04* (2013.01); *A61K 31/7028* (2013.01); *A61K 31/739* (2013.01); *A61K 47/65* (2017.08); *A61P 31/12* (2018.01); *A61P 35/00* (2018.01); *A61P 37/04* (2018.01); *C07H 15/06* (2013.01); *C07H 15/18* (2013.01)

(58) Field of Classification Search
CPC ......... C07H 15/04; C07H 15/06; C07H 15/18
See application file for complete search history.

(56) References Cited

U.S. PATENT DOCUMENTS

| | | | | |
|---|---|---|---|---|
| 2009/0239813 A1 | | 9/2009 | Cerundolo et al. | |
| 2012/0178705 A1 | * | 7/2012 | Liang .................... | C07H 15/18<br>514/25 |
| 2012/0269857 A1 | | 10/2012 | Cerundolo et al. | |
| 2015/0191503 A1 | | 7/2015 | Compton et al. | |

OTHER PUBLICATIONS

PUBCHEM: Substance Record for SID 228720835, U.S. National Library of Medicine, National Center for Biotechnology Information, Feb. 12, 2015, pp. 1-7, accessed Jan. 6, 2017.
Patent Cooperation Treaty, International Search Report for PCT/US2016/061861, dated Jan. 24, 2017, pp. 1-4.

* cited by examiner

*Primary Examiner* — Pancham Bakshi
(74) *Attorney, Agent, or Firm* — Pillsbury Winthrop Shaw Pittman LLP

(57) ABSTRACT

The compounds, compositions and methods provided herein antagonize, inhibit, decrease, reduce, suppress, or disrupt CD1d-mediated, iNKT cell-mediated, and/or iNKT cell TCR-mediated immune signaling. The sphingamide compounds were rationally designed based upon 3D structural considerations in relation to the structures of each of CD1d, the iNKT cell TCR, and the ternary complex CD1d-a-GalCer analog lipids-TCR. More specifically, the addition of an amide in the phytosphingosine tail of a derivative of α-GalCer led to a non-conserved binding with CD1d, a conserved binding with the iNKT cell TCR, and an antagonist-like phenotype.

16 Claims, 13 Drawing Sheets

Specification includes a Sequence Listing.

SEQUENCE LISTING

<160> NUMBER OF SEQ ID NOS: 10

<210> SEQ ID NO 1
<211> LENGTH: 336
<212> TYPE: PRT
<213> ORGANISM: Mus musculus

<400> SEQUENCE: 1

| Met | Arg | Tyr | Leu | Pro | Trp | Leu | Leu | Leu | Trp | Ala | Phe | Leu | Gln | Val | Trp |
|---|---|---|---|---|---|---|---|---|---|---|---|---|---|---|---|
| 1 | | | | 5 | | | | | 10 | | | | | 15 | |

| Gly | Gln | Ser | Glu | Ala | Gln | Gln | Lys | Asn | Tyr | Thr | Phe | Arg | Cys | Leu | Gln |
| | | | 20 | | | | | 25 | | | | | 30 | | |

| Met | Ser | Ser | Phe | Ala | Asn | Arg | Ser | Trp | Ser | Arg | Thr | Asp | Ser | Val | Val |
| | | 35 | | | | | 40 | | | | | 45 | | | |

| Trp | Leu | Gly | Asp | Leu | Gln | Thr | His | Arg | Trp | Ser | Asn | Asp | Ser | Ala | Thr |
| | 50 | | | | | 55 | | | | | 60 | | | | |

| Ile | Ser | Phe | Thr | Lys | Pro | Trp | Ser | Gln | Gly | Lys | Leu | Ser | Asn | Gln | Gln |
| 65 | | | | | 70 | | | | | 75 | | | | | 80 |

| Trp | Glu | Lys | Leu | Gln | His | Met | Phe | Gln | Val | Tyr | Arg | Val | Ser | Phe | Thr |
| | | | | 85 | | | | | 90 | | | | | 95 | |

| Arg | Asp | Ile | Gln | Glu | Leu | Val | Lys | Met | Met | Ser | Pro | Lys | Glu | Asp | Tyr |
| | | | 100 | | | | | 105 | | | | | 110 | | |

| Pro | Ile | Glu | Ile | Gln | Leu | Ser | Ala | Gly | Cys | Glu | Met | Tyr | Pro | Gly | Asn |
| | | | | 115 | | | | | 120 | | | | | 125 | |

| Ala | Ser | Glu | Ser | Phe | Leu | His | Val | Ala | Phe | Gln | Gly | Lys | Tyr | Val | Val |
| | | 130 | | | | | 135 | | | | | 140 | | | |

| Arg | Phe | Trp | Gly | Thr | Ser | Trp | Gln | Thr | Val | Pro | Gly | Ala | Pro | Ser | Trp |
| 145 | | | | | 150 | | | | | 155 | | | | | 160 |

| Leu | Asp | Leu | Pro | Ile | Lys | Val | Leu | Asn | Ala | Asp | Gln | Gly | Thr | Ser | Ala |
| | | | | 165 | | | | | 170 | | | | | 175 | |

| Thr | Val | Gln | Met | Leu | Leu | Asn | Asp | Thr | Cys | Pro | Leu | Phe | Val | Arg | Gly |
| | | | 180 | | | | | 185 | | | | | 190 | | |

| Leu | Leu | Glu | Ala | Gly | Lys | Ser | Asp | Leu | Glu | Lys | Gln | Glu | Lys | Pro | Val |
| | | | | 195 | | | | | 200 | | | | | 205 | |

| Ala | Trp | Leu | Ser | Ser | Val | Pro | Ser | Ser | Ala | Asp | Gly | His | Arg | Gln | Leu |
| | | 210 | | | | | 215 | | | | | 220 | | | |

| Val | Cys | His | Val | Ser | Gly | Phe | Tyr | Pro | Lys | Pro | Val | Trp | Val | Met | Trp |
| 225 | | | | | 230 | | | | | 235 | | | | | 240 |

| Met | Arg | Gly | Asp | Gln | Glu | Gln | Gln | Gly | Thr | His | Arg | Gly | Asp | Phe | Leu |
| | | | | 245 | | | | | 250 | | | | | 255 | |

| Pro | Asn | Ala | Asp | Glu | Thr | Trp | Tyr | Leu | Gln | Ala | Thr | Leu | Asp | Val | Glu |
| | | | 260 | | | | | 265 | | | | | 270 | | |

| Ala | Gly | Glu | Glu | Ala | Gly | Leu | Ala | Cys | Arg | Val | Lys | His | Ser | Ser | Leu |
| | | 275 | | | | | 280 | | | | | 285 | | | |

| Gly | Gly | Gln | Asp | Ile | Ile | Leu | Tyr | Trp | Asp | Ala | Arg | Gln | Ala | Pro | Val |
| | | 290 | | | | | 295 | | | | | 300 | | | |

| Gly | Leu | Ile | Val | Phe | Ile | Val | Leu | Ile | Met | Leu | Val | Val | Val | Gly | Ala |
| 305 | | | | | 310 | | | | | 315 | | | | | 320 |

| Val | Val | Tyr | Tyr | Ile | Trp | Arg | Arg | Ser | Ala | Tyr | Gln | Asp | Ile | Arg |
| | | | | 325 | | | | | 330 | | | | | 335 |

<210> SEQ ID NO 2
<211> LENGTH: 318
<212> TYPE: PRT
<213> ORGANISM: Mus musculus

```
<400> SEQUENCE: 2

Ser Glu Ala Gln Gln Lys Asn Tyr Thr Phe Arg Cys Leu Gln Met Ser
1               5                   10                  15

Ser Phe Ala Asn Arg Ser Trp Ser Arg Thr Asp Ser Val Val Trp Leu
            20                  25                  30

Gly Asp Leu Gln Thr His Arg Trp Ser Asn Asp Ser Ala Thr Ile Ser
            35                  40                  45

Phe Thr Lys Pro Trp Ser Gln Gly Lys Leu Ser Asn Gln Gln Trp Glu
            50                  55                  60

Lys Leu Gln His Met Phe Gln Val Tyr Arg Val Ser Phe Thr Arg Asp
65                  70                  75                  80

Ile Gln Glu Leu Val Lys Met Met Ser Pro Lys Glu Asp Tyr Pro Ile
                85                  90                  95

Glu Ile Gln Leu Ser Ala Gly Cys Glu Met Tyr Pro Gly Asn Ala Ser
            100                 105                 110

Glu Ser Phe Leu His Val Ala Phe Gln Gly Lys Tyr Val Val Arg Phe
            115                 120                 125

Trp Gly Thr Ser Trp Gln Thr Val Pro Gly Ala Pro Ser Trp Leu Asp
130                 135                 140

Leu Pro Ile Lys Val Leu Asn Ala Asp Gln Gly Thr Ser Ala Thr Val
145                 150                 155                 160

Gln Met Leu Leu Asn Asp Thr Cys Pro Leu Phe Val Arg Gly Leu Leu
                165                 170                 175

Glu Ala Gly Lys Ser Asp Leu Glu Lys Gln Glu Lys Pro Val Ala Trp
            180                 185                 190

Leu Ser Ser Val Pro Ser Ser Ala Asp Gly His Arg Gln Leu Val Cys
            195                 200                 205

His Val Ser Gly Phe Tyr Pro Lys Pro Val Trp Val Met Trp Met Arg
            210                 215                 220

Gly Asp Gln Glu Gln Gln Gly Thr His Arg Gly Asp Phe Leu Pro Asn
225                 230                 235                 240

Ala Asp Glu Thr Trp Tyr Leu Gln Ala Thr Leu Asp Val Glu Ala Gly
                245                 250                 255

Glu Glu Ala Gly Leu Ala Cys Arg Val Lys His Ser Ser Leu Gly Gly
            260                 265                 270

Gln Asp Ile Ile Leu Tyr Trp Asp Ala Arg Gln Ala Pro Val Gly Leu
            275                 280                 285

Ile Val Phe Ile Val Leu Ile Met Leu Val Val Val Gly Ala Val Val
            290                 295                 300

Tyr Tyr Ile Trp Arg Arg Arg Ser Ala Tyr Gln Asp Ile Arg
305                 310                 315

<210> SEQ ID NO 3
<211> LENGTH: 335
<212> TYPE: PRT
<213> ORGANISM: homo sapiens

<400> SEQUENCE: 3

Met Gly Cys Leu Leu Phe Leu Leu Leu Trp Ala Leu Leu Gln Ala Trp
1               5                   10                  15

Gly Ser Ala Glu Val Pro Gln Arg Leu Phe Pro Leu Arg Cys Leu Gln
            20                  25                  30

Ile Ser Ser Phe Ala Asn Ser Ser Trp Thr Arg Thr Asp Gly Leu Ala
            35                  40                  45
```

-continued

```
Trp Leu Gly Glu Leu Gln Thr His Ser Trp Ser Asn Asp Ser Asp Thr
 50                  55                  60

Val Arg Ser Leu Lys Pro Trp Ser Gln Gly Thr Phe Ser Asp Gln Gln
 65                  70                  75                  80

Trp Glu Thr Leu Gln His Ile Phe Arg Val Tyr Arg Ser Ser Phe Thr
                 85                  90                  95

Arg Asp Val Lys Glu Phe Ala Lys Met Leu Arg Leu Ser Tyr Pro Leu
                100                 105                 110

Glu Leu Gln Val Ser Ala Gly Cys Glu Val His Pro Gly Asn Ala Ser
            115                 120                 125

Asn Asn Phe Phe His Val Ala Phe Gln Gly Lys Asp Ile Leu Ser Phe
130                 135                 140

Gln Gly Thr Ser Trp Glu Pro Thr Gln Glu Ala Pro Leu Trp Val Asn
145                 150                 155                 160

Leu Ala Ile Gln Val Leu Asn Gln Asp Lys Trp Thr Arg Glu Thr Val
                165                 170                 175

Gln Trp Leu Leu Asn Gly Thr Cys Pro Gln Phe Val Ser Gly Leu Leu
            180                 185                 190

Glu Ser Gly Lys Ser Glu Leu Lys Lys Gln Val Lys Pro Lys Ala Trp
        195                 200                 205

Leu Ser Arg Gly Pro Ser Pro Gly Pro Gly Arg Leu Leu Leu Val Cys
210                 215                 220

His Val Ser Gly Phe Tyr Pro Lys Pro Val Trp Val Lys Trp Met Arg
225                 230                 235                 240

Gly Glu Gln Glu Gln Gln Gly Thr Gln Pro Gly Asp Ile Leu Pro Asn
                245                 250                 255

Ala Asp Glu Thr Trp Tyr Leu Arg Ala Thr Leu Asp Val Val Ala Gly
            260                 265                 270

Glu Ala Ala Gly Leu Ser Cys Arg Val Lys His Ser Ser Leu Glu Gly
        275                 280                 285

Gln Asp Ile Val Leu Tyr Trp Gly Gly Ser Tyr Thr Ser Met Gly Leu
    290                 295                 300

Ile Ala Leu Ala Val Leu Ala Cys Leu Leu Phe Leu Leu Ile Val Gly
305                 310                 315                 320

Phe Thr Ser Arg Phe Lys Arg Gln Thr Ser Tyr Gln Gly Val Leu
                325                 330                 335

<210> SEQ ID NO 4
<211> LENGTH: 315
<212> TYPE: PRT
<213> ORGANISM: homo sapiens

<400> SEQUENCE: 4

Val Pro Gln Arg Leu Phe Pro Leu Arg Cys Leu Gln Ile Ser Ser Phe
 1               5                  10                  15

Ala Asn Ser Ser Trp Thr Arg Thr Asp Gly Leu Ala Trp Leu Gly Glu
                20                  25                  30

Leu Gln Thr His Ser Trp Ser Asn Asp Ser Asp Thr Val Arg Ser Leu
            35                  40                  45

Lys Pro Trp Ser Gln Gly Thr Phe Ser Asp Gln Gln Trp Glu Thr Leu
        50                  55                  60

Gln His Ile Phe Arg Val Tyr Arg Ser Ser Phe Thr Arg Asp Val Lys
 65                  70                  75                  80

Glu Phe Ala Lys Met Leu Arg Leu Ser Tyr Pro Leu Glu Leu Gln Val
                85                  90                  95
```

Ser Ala Gly Cys Glu Val His Pro Gly Asn Ala Ser Asn Phe Phe
            100                 105                 110

His Val Ala Phe Gln Gly Lys Asp Ile Leu Ser Phe Gln Gly Thr Ser
            115                 120                 125

Trp Glu Pro Thr Gln Glu Ala Pro Leu Trp Val Asn Leu Ala Ile Gln
130                 135                 140

Val Leu Asn Gln Asp Lys Trp Thr Arg Glu Thr Val Gln Trp Leu Leu
145                 150                 155                 160

Asn Gly Thr Cys Pro Gln Phe Val Ser Gly Leu Leu Glu Ser Gly Lys
                165                 170                 175

Ser Glu Leu Lys Lys Gln Val Lys Pro Lys Ala Trp Leu Ser Arg Gly
            180                 185                 190

Pro Ser Pro Gly Pro Gly Arg Leu Leu Leu Val Cys His Val Ser Gly
            195                 200                 205

Phe Tyr Pro Lys Pro Val Trp Val Lys Trp Met Arg Gly Glu Gln Glu
            210                 215                 220

Gln Gln Gly Thr Gln Pro Gly Asp Ile Leu Pro Asn Ala Asp Glu Thr
225                 230                 235                 240

Trp Tyr Leu Arg Ala Thr Leu Asp Val Val Ala Gly Glu Ala Ala Gly
                245                 250                 255

Leu Ser Cys Arg Val Lys His Ser Ser Leu Glu Gly Gln Asp Ile Val
            260                 265                 270

Leu Tyr Trp Gly Gly Ser Tyr Thr Ser Met Gly Leu Ile Ala Leu Ala
            275                 280                 285

Val Leu Ala Cys Leu Leu Phe Leu Leu Ile Val Gly Phe Thr Ser Arg
            290                 295                 300

Phe Lys Arg Gln Thr Ser Tyr Gln Gly Val Leu
305                 310                 315

<210> SEQ ID NO 5
<211> LENGTH: 272
<212> TYPE: PRT
<213> ORGANISM: Mus musculus

<400> SEQUENCE: 5

Met Lys Lys Arg Leu Ser Ala Cys Trp Val Val Leu Trp Leu His Tyr
1               5                   10                  15

Gln Trp Val Ala Gly Lys Thr Gln Val Glu Gln Ser Pro Gln Ser Leu
            20                  25                  30

Val Val Arg Gln Gly Glu Asn Cys Val Leu Gln Cys Asn Tyr Ser Val
            35                  40                  45

Thr Pro Asp Asn His Leu Arg Trp Phe Lys Gln Asp Thr Gly Lys Gly
50                  55                  60

Leu Val Ser Leu Thr Val Leu Val Asp Gln Lys Asp Lys Thr Ser Asn
65                  70                  75                  80

Gly Arg Tyr Ser Ala Thr Leu Asp Lys Asp Ala Lys His Ser Thr Leu
                85                  90                  95

His Ile Thr Ala Thr Leu Leu Asp Asp Thr Ala Thr Tyr Ile Cys Val
            100                 105                 110

Val Gly Asp Arg Gly Ser Ala Leu Gly Arg Leu His Phe Gly Ala Gly
            115                 120                 125

Thr Gln Leu Ile Val Ile Pro Asp Ile Gln Asn Pro Glu Pro Ala Val
130                 135                 140

Tyr Gln Leu Lys Asp Pro Arg Ser Gln Asp Ser Thr Leu Cys Leu Phe

```
                145                 150                 155                 160
Thr Asp Phe Asp Ser Gln Ile Asn Val Pro Lys Thr Met Glu Ser Gly
                    165                 170                 175
Thr Phe Ile Thr Asp Lys Thr Val Leu Asp Met Lys Ala Met Asp Ser
                180                 185                 190
Lys Ser Asn Gly Ala Ile Ala Trp Ser Asn Gln Thr Ser Phe Thr Cys
                195                 200                 205
Gln Asp Ile Phe Lys Glu Thr Asn Ala Thr Tyr Pro Ser Ser Asp Val
            210                 215                 220
Pro Cys Asp Ala Thr Leu Thr Glu Lys Ser Phe Glu Thr Asp Met Asn
225                 230                 235                 240
Leu Asn Phe Gln Asn Leu Ser Val Met Gly Leu Arg Ile Leu Leu Leu
                245                 250                 255
Lys Val Ala Gly Phe Asn Leu Leu Met Thr Leu Arg Leu Trp Ser Ser
                260                 265                 270

<210> SEQ ID NO 6
<211> LENGTH: 304
<212> TYPE: PRT
<213> ORGANISM: Mus musculus

<400> SEQUENCE: 6

Met Gly Ser Arg Leu Phe Phe Val Leu Ser Leu Leu Cys Ser Lys
1               5                   10                  15
His Met Glu Ala Ala Val Thr Gln Ser Pro Arg Asn Lys Val Ala Val
                20                  25                  30
Thr Gly Gly Lys Val Thr Leu Ser Cys Asn Gln Thr Asn Asn His Asn
            35                  40                  45
Asn Met Tyr Trp Tyr Arg Gln Asp Thr Gly His Gly Leu Arg Leu Ile
        50                  55                  60
His Tyr Ser Tyr Gly Ala Gly Ser Thr Glu Lys Gly Asp Ile Pro Asp
65                  70                  75                  80
Gly Tyr Lys Ala Ser Arg Pro Ser Gln Glu Asn Phe Ser Leu Ile Leu
                85                  90                  95
Glu Leu Ala Thr Pro Ser Gln Thr Ser Val Tyr Phe Cys Ala Ser Gly
                100                 105                 110
Glu Gly Gly Leu Gly Gly Pro Thr Gln Tyr Phe Gly Pro Gly Thr Arg
            115                 120                 125
Leu Leu Val Leu Glu Asp Leu Arg Asn Val Thr Pro Pro Lys Val Ser
        130                 135                 140
Leu Phe Glu Pro Ser Lys Ala Glu Ile Ala Asn Lys Gln Lys Ala Thr
145                 150                 155                 160
Leu Val Cys Leu Ala Arg Gly Phe Phe Pro Asp His Val Glu Leu Ser
                165                 170                 175
Trp Trp Val Asn Gly Lys Glu Val His Ser Gly Val Ser Thr Asp Pro
                180                 185                 190
Gln Ala Tyr Lys Glu Ser Asn Tyr Ser Tyr Cys Leu Ser Ser Arg Leu
            195                 200                 205
Arg Val Ser Ala Thr Phe Trp His Asn Pro Arg Asn His Phe Arg Cys
        210                 215                 220
Gln Val Gln Phe His Gly Leu Ser Glu Glu Asp Lys Trp Pro Glu Gly
225                 230                 235                 240
Ser Pro Lys Pro Val Thr Gln Asn Ile Ser Ala Glu Ala Trp Gly Arg
                245                 250                 255
```

-continued

Ala Asp Cys Gly Ile Thr Ser Ala Ser Tyr His Gln Gly Val Leu Ser
            260                 265                 270

Ala Thr Ile Leu Tyr Glu Ile Leu Leu Gly Lys Ala Thr Leu Tyr Ala
            275                 280                 285

Val Leu Val Ser Gly Leu Val Leu Arg Pro Gly Gln Glu Lys Asn Ser
            290                 295                 300

<210> SEQ ID NO 7
<211> LENGTH: 298
<212> TYPE: PRT
<213> ORGANISM: Mus musculus

<400> SEQUENCE: 7

Met Arg Val Arg Leu Ile Ser Ala Val Val Leu Cys Phe Leu Gly Thr
1               5                   10                  15

Gly Leu Val Asp Met Lys Val Thr Gln Met Pro Arg Tyr Leu Ile Lys
            20                  25                  30

Arg Met Gly Glu Asn Val Leu Leu Glu Cys Gly Gln Asp Met Ser His
        35                  40                  45

Glu Thr Met Tyr Trp Tyr Arg Gln Asp Pro Gly Leu Gly Leu Gln Leu
    50                  55                  60

Ile Tyr Ile Ser Tyr Asp Val Asp Ser Asn Ser Glu Gly Asp Ile Pro
65                  70                  75                  80

Lys Gly Tyr Arg Val Ser Arg Lys Lys Arg Glu His Phe Ser Leu Ile
                85                  90                  95

Leu Asp Ser Ala Lys Thr Asn Gln Thr Ser Val Tyr Phe Cys Ala Ser
            100                 105                 110

Ser Leu Arg Gly Gln Asn Thr Leu Tyr Phe Gly Ala Gly Thr Arg Leu
        115                 120                 125

Ser Val Leu Glu Asp Leu Arg Asn Val Thr Pro Pro Lys Val Ser Leu
    130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr His Gln Gly Val Leu Ser Ala
            260                 265                 270

Thr Ile Leu Tyr Glu Ile Leu Leu Gly Lys Gly His Pro Ile Cys Cys
        275                 280                 285

Ala Gly Gln Trp Pro Ser Ala Asp Glu Gly
    290                 295

<210> SEQ ID NO 8
<211> LENGTH: 119
<212> TYPE: PRT
<213> ORGANISM: Mus musculus

<400> SEQUENCE: 8

```
Leu Leu Glu Gln Asn Pro Arg Trp Arg Leu Val Pro Arg Gly Gln Ala
1               5                   10                  15

Val Asn Leu Arg Cys Ile Leu Lys Asn Ser Gln Tyr Pro Trp Met Ser
            20                  25                  30

Trp Tyr Gln Gln Asp Leu Gln Lys Gln Leu Gln Trp Leu Phe Thr Leu
        35                  40                  45

Arg Ser Pro Gly Asp Lys Glu Val Lys Ser Leu Pro Gly Ala Asp Tyr
    50                  55                  60

Leu Ala Thr Arg Val Thr Asp Thr Glu Leu Arg Leu Gln Val Ala Asn
65                  70                  75                  80

Met Ser Gln Gly Arg Thr Leu Tyr Cys Thr Cys Ser Ala Arg Leu Gly
                85                  90                  95

Asp Asn Gln Asp Thr Gln Tyr Phe Gly Pro Gly Thr Arg Leu Leu Val
            100                 105                 110

Leu Glu Asp Leu Arg Asn Val
        115
```

<210> SEQ ID NO 9
<211> LENGTH: 276
<212> TYPE: PRT
<213> ORGANISM: Homo sapiens

<400> SEQUENCE: 9

```
Met Lys Lys His Leu Thr Thr Phe Leu Val Ile Leu Trp Leu Tyr Phe
1               5                   10                  15

Tyr Arg Gly Asn Gly Lys Asn Gln Val Glu Gln Ser Pro Gln Ser Leu
            20                  25                  30

Ile Ile Leu Glu Gly Lys Asn Cys Thr Leu Gln Cys Asn Tyr Thr Val
        35                  40                  45

Ser Pro Phe Ser Asn Leu Arg Trp Tyr Lys Gln Asp Thr Gly Arg Gly
    50                  55                  60

Pro Val Ser Leu Thr Ile Met Thr Phe Ser Glu Asn Thr Lys Ser Asn
65                  70                  75                  80

Gly Arg Tyr Thr Ala Thr Leu Asp Ala Asp Thr Lys Gln Ser Ser Leu
                85                  90                  95

His Ile Thr Ala Ser Gln Leu Ser Asp Ser Ala Ser Tyr Ile Cys Val
            100                 105                 110

Val Ser Asp Arg Gly Ser Thr Leu Gly Arg Leu Tyr Phe Gly Arg Gly
        115                 120                 125

Thr Gln Leu Thr Val Trp Pro Asp Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240
```

```
Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275

<210> SEQ ID NO 10
<211> LENGTH: 313
<212> TYPE: PRT
<213> ORGANISM: Homo sapiens

<400> SEQUENCE: 10

Met Ser Thr Arg Leu Leu Cys Tyr Val Gly Phe Tyr Phe Leu Gly Ala
1               5                   10                  15

Gly Leu Met Glu Ala Asp Ile Tyr Gln Thr Pro Arg Tyr Leu Val Ile
            20                  25                  30

Gly Thr Gly Lys Lys Ile Thr Leu Glu Cys Ser Gln Thr Met Gly His
        35                  40                  45

Asp Lys Met Tyr Trp Tyr Gln Gln Asp Pro Gly Met Glu Leu His Leu
50                  55                  60

Ile His Tyr Ser Tyr Gly Val Asn Ser Thr Glu Lys Gly Asp Leu Ser
65                  70                  75                  80

Ser Glu Ser Thr Val Ser Arg Ile Arg Thr Glu His Phe Pro Leu Thr
                85                  90                  95

Leu Glu Ser Ala Arg Pro Ser His Thr Ser Gln Tyr Leu Cys Ala Ser
            100                 105                 110

Ser Ala Lys Asp Arg Gln Val Ser Ser Gln Glu Thr Gln Tyr Phe Gly
        115                 120                 125

Pro Gly Thr Arg Leu Leu Val Leu Glu Asp Leu Lys Asn Val Phe Pro
130                 135                 140

Pro Glu Val Ala Val Phe Glu Pro Ser Glu Ala Glu Ile Ser His Thr
145                 150                 155                 160

Gln Lys Ala Thr Leu Val Cys Leu Ala Thr Gly Phe Tyr Pro Asp His
                165                 170                 175

Val Glu Leu Ser Trp Trp Val Asn Gly Lys Glu Val His Ser Gly Val
            180                 185                 190

Ser Thr Asp Pro Gln Pro Leu Lys Glu Gln Pro Ala Leu Asn Asp Ser
        195                 200                 205

Arg Tyr Cys Leu Ser Ser Arg Leu Arg Val Ser Ala Thr Phe Trp Gln
210                 215                 220

Asn Pro Arg Asn His Phe Arg Cys Gln Val Gln Phe Tyr Gly Leu Ser
225                 230                 235                 240

Glu Asn Asp Glu Trp Thr Gln Asp Arg Ala Lys Pro Val Thr Gln Ile
                245                 250                 255

Val Ser Ala Glu Ala Trp Gly Arg Ala Asp Cys Gly Phe Thr Ser Val
            260                 265                 270

Ser Tyr Gln Gln Gly Val Leu Ser Ala Thr Ile Leu Tyr Glu Ile Leu
        275                 280                 285

Leu Gly Lys Ala Thr Leu Tyr Ala Val Leu Val Ser Ala Leu Val Leu
        290                 295                 300

Met Ala Met Val Lys Arg Lys Asp Phe
305                 310
```

SPHINGAMIDE COMPOUNDS AND METHODS FOR BINDING INKT CELLS

RELATED APPLICATIONS

This application is the National Phase of International Application No. PCT/US2016/061861, filed Nov. 14, 2016 which designated the U.S. and that International Application was published under PCT Article 21(2) in English, and claims priority to U.S. Provisional Patent Application No. 62/254,973 filed Nov. 13, 2015. The entire contents of the foregoing applications are incorporated herein by reference, including all text, tables and drawings.

SEQUENCE LISTING

The present application is being filed with a Sequence Listing. The Sequence Listing is submitted electronically in in ASCII format via EFS-Web in the form of a text file. Said ASCII copy, created on May 10, 2018, is named LIAI-0459133-Seq-Listing_ST25.txt and is 25.1 KB in size, the contents of which are incorporated herein by reference in their entirety.

INTRODUCTION

Invariant natural killer T cells (iNKT) are a subset of regulatory T cells with features of both innate and adaptive immunity. In contrast to conventional T cells that are activated by a peptide presented by an MHC class I or class II molecule, iNKT cells recognize lipid derivatives presented by the glycoprotein cluster differentiation 1 type d (CD1d), a non-classical MHC I molecule presented on antigen presenting cells.

Activation of iNKT cells by agonist ligands in vivo is initiated by TCR engagement of CD1d-expressing antigen presenting cells (APCs), including dendritic cells (DCs), macrophages and B cells, and results in immediate reciprocal activation of the APC, through CD40L-CD40 upregulation and interaction, and NK cells. These early events and the massive release of Th1 and Th2 cytokines and chemokines by activated iNKT cells underlie the powerful adjuvant properties of these agonists for CD4+, CD8+ T cell and B cell immunity. iNKT cell activation results in cytotoxicity, proliferation, and also rapid cytokine production (within several hours), which subsequently activate several bystander immune cells (natural killer cells, dendritic cells, B cells etc.) iNKT cells have the capacity to produce both Th1 and Th2 cytokines and to modulate cytokine production by bystander cells. Co-stimulatory molecules also play an important role in the polarization of the Th1 or Th2 response.

Activation of iNKT cells ameliorates some conditions and exacerbates others. For instance the release of interferon gamma (IFN-γ) from an activated iNKT cell may ameliorate bacterial, parasitic or viral infections, and assist with tumor rejection, but simultaneously exacerbate atherosclerosis or graft vs host disease. Similarly the release of interleukin 4/13 (IL-4/13) from activated iNKT cells may assist with autoimmune disease, diabetes, experimental autoimmune encephalomyelitis (EAE), or autoimmune hepatitis, but exacerbate other autoimmune diseases, airway hyperactivity, contact hypersensitivity or ulcerative colitis. Accordingly, methods of modifying the cytokine cascade or signal transduction of iNKT cells is of particular interest for therapeutic and preventative purposes. However, a sphingamide antagonist of CD1d-mediated, iNKT cell-mediated, or iNKT cell TCR-mediated signaling has not, until now, been described. Accordingly there is a need for modifying the cytokine cascade or signal transduction of iNKT cells in patients in need thereof. The present embodiments provide compounds, compositions and methods.

SUMMARY

The present embodiments are directed to compounds, compositions and methods that advantageously employ analogs of α-GalCer, in particular, sphingamides to modify CD1d-mediated, iNKT cell-mediated, or iNKT cell TCR-mediated signaling. According to a first embodiment described herein, the present disclosures provides sphingamide compounds having a structure including formula I, or pharmaceutically acceptable salt thereof, or a prodrug thereof:

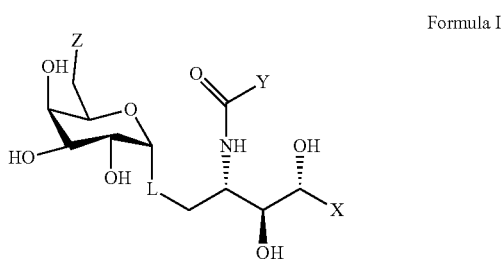

Formula I wherein X represents an alkyl chain having 5 to 30 carbons and at least one amide group, wherein the alkyl chain may be substituted by one or more O, S, or P atoms, or a 4 to 6 membered homo- or heterocyclic ring, wherein the heteroatoms, if present, are selected from either O or N and the ring may be substituted with a halogen atom;
wherein Y is an alkyl chain having 5 to 30 carbons and the alkyl chain having 5 to 30 carbons is optionally terminated with a 4 to 6 membered homo- or heterocyclic ring, and the heteroatoms, if present, are selected from either an O or an N atom and the ring may be substituted with a halogen atom;
wherein Z represents a group selected from an —OH, a 2-naphtureido, a phenylureido, a benzyl amide, a 4-pyridinylcarbamoyl, or a 2-napthylcarbamoyl; and,
wherein L represents a linker selected from an oxygen atom or a lower alkyl group.

Embodiments described herein include compounds according to the first embodiment having the structure of formula II, or a pharmaceutically acceptable salt thereof, or a prodrug thereof:

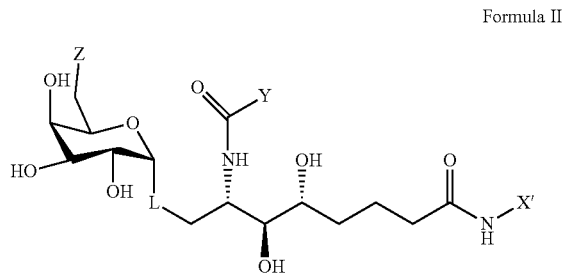

Formula II wherein X' is an alkyl chain having two to 8 carbons, one or two carbons optionally substituted with O or a 4 to 6 membered homo- or heterocyclic ring, and the heteroatoms, if present, are selected from either O or N and the ring may be substituted with a halogen atom, wherein the alkyl chain is optionally terminated with a 4 to 6 membered homo- or heterocyclic ring, and the heteroatoms, if present, are selected from either O or N and the ring may be substituted with a halogen atom, wherein Y and Z are described above, and wherein L represents either an oxygen atom or $CH_2$.

In a particular aspect of this second embodiment, the X' is selected from the group consisting of:

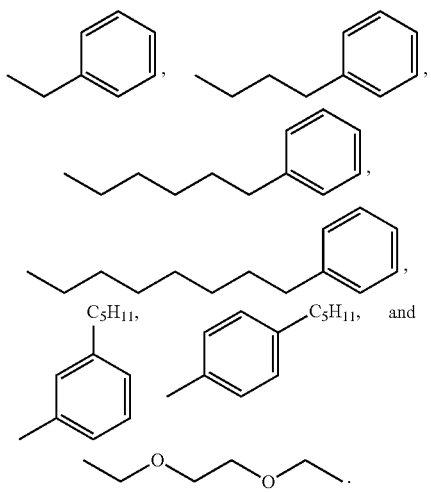

In a further aspect of either the first embodiment, or the further embodiment, Y is selected from the group consisting of:

a $C_{27}H_{55}$ unbranched alkyl chain;
a $C_{25}H_{51}$ unbranched alkyl chain;
a $C_{23}H_{47}$ unbranched alkyl chain;
a $C_7H_{15}$ unbranched alkyl chain; and

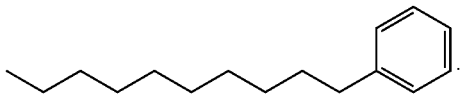 [SMILES: CCCCCCCCCCc1ccccc1]

In yet a further aspect, the Z of any of the first or second embodiments, or preceding aspects thereof may be selected from the group consisting of:
an —OH group,

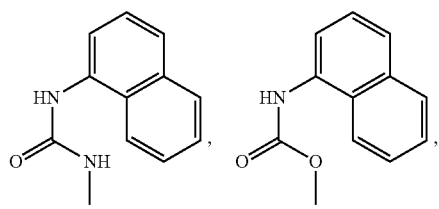

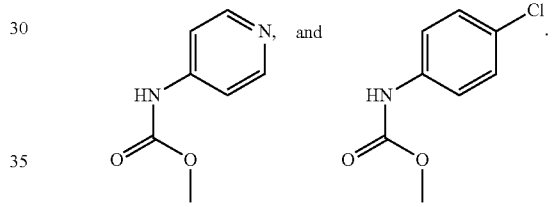

In very particular aspect, the compounds of interest include at least the following compounds, their prodrugs or pharmaceutically acceptable salts thereof:

JG081

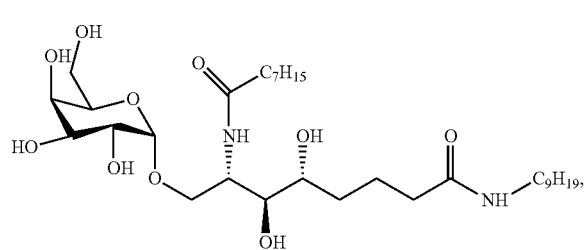

JG079

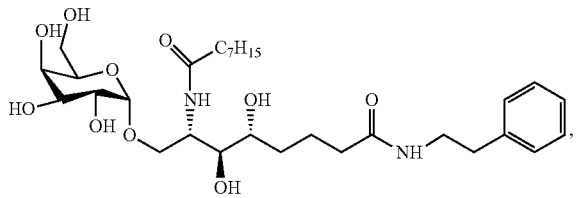

JG172

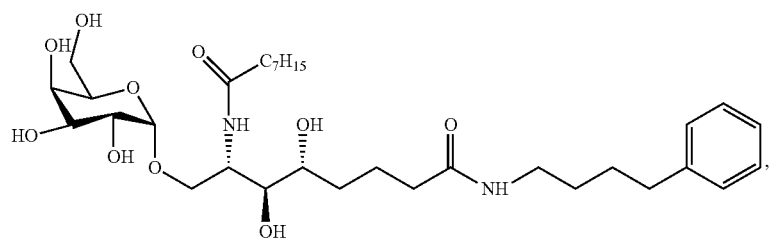

-continued

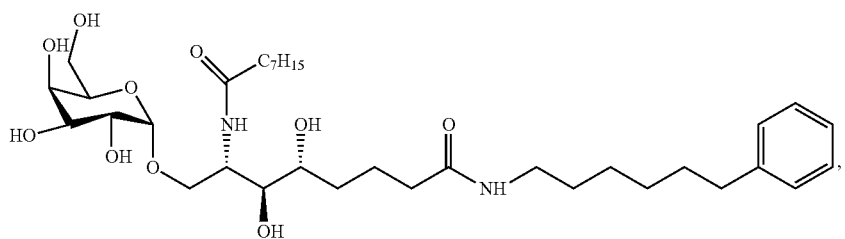
JG168

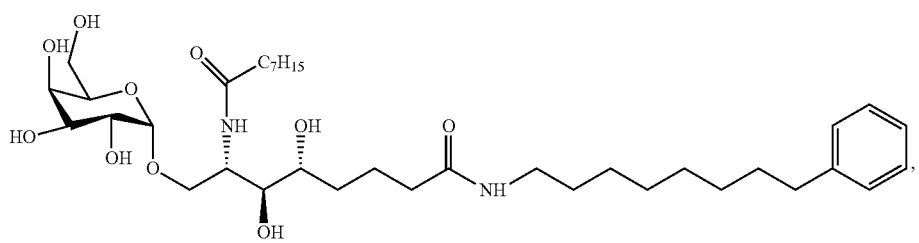
JG254

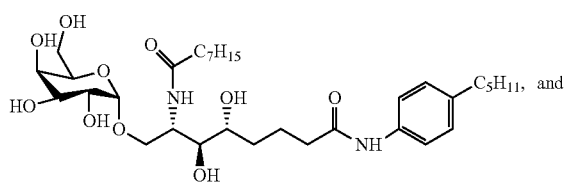
JG076

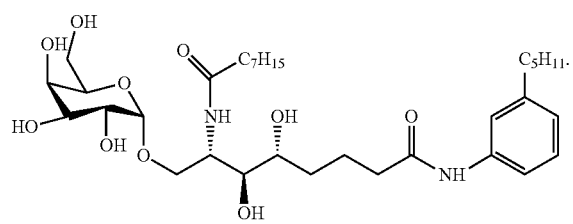
JG143

In some embodiment of any of the preceding compounds, the compound may bind one or more of CD1 or an NKT cell TCR. In one aspect, the CD1 is CD1d and the NKT cell TCR is an iNKT cell TCR. In an even more particular aspect, the CD1d is a mouse or human CD1d and the iNKT cell TCR is a mouse or human iNKT cell TCR. Yet even more particularly, the mouse CD1d may have the amino acid sequence of SEQ ID NO: 2 or a sequence having substantial identity thereto, and the human CD1d sequence may have the amino acid sequence of SEQ ID NO: 4 or a sequence having substantial identity thereto.

Specific examples of TCRs to be bound by any of the preceding compounds include iNKT cell TCRs from at least one of the following murine hybridomas DN3A4-1.2 (Vα14Vβ8.2), DN3A4-1.4 (Vα14Vβ10), N38.2H4 (Vα14Vβ7) and DN32.D3 (Vα14Vβ8.2).

In a particular aspect, a compound of any of the embodiments discussed above may bind an iNKT cell TCR having the amino acid sequence of one or more of SEQ ID NOs: 5, 6, 7, 8, 9 or 10, or an amino acid sequence substantially identical to any of SEQ ID NOs: 5, 6, 7, 8, 9, or 10.

In a further aspect, the compound of any of the preceding embodiments may bind CD1d in a non-conserved manner when compared to the binding of α-GalCer. Furthermore, the compound may bind an iNKT cell TCR in a conserved manner when compared to the binding of α-GalCer.

In yet another aspect, the compounds described in any of the preceding embodiments may generate hydrogen bonds with mCD1d (SEQ ID NO: 2) or a sequence having substantial identity thereto at amino acid residues D80 and D153. At least some of the compounds of this aspect may further generate a hydrogen bond with mCD1d (SEQ ID NO: 2) or a sequence having substantial identity thereto at amino acid residue Y73 when the compound is also bound to an iNKT cell TCR.

In a further aspect, a compound of any of the preceding embodiments or aspects may generate hydrogen bonds with mouse Vα14Vβ8.2 iNKT cell TCR (SEQ ID NO: 6), or a sequence having substantial identity thereto at amino acid residues N30, G96, and R95.

In yet another aspect, a compound of any of the preceding embodiments or aspects thereto may have a binding affinity to CD1d or the iNKT cell TCR is in the nanomolar range or micromolar range.

Embodiments described herein include compositions comprising the compound of any of the preceding embodiments (or aspects thereof) and one or more additional active ingredients and/or one or more inactive ingredients. In one particular aspect, the active ingredient is a spacer lipid.

Embodiments described herein include a therapeutic composition comprising any of the first or second embodiments (or aspects thereof) as an active ingredient and a pharmaceutically acceptable carrier.

Embodiments described herein include a method of treating an immunomodulatory disease comprising administering the composition of the third or fourth embodiments to a patient in need thereof.

Embodiments described herein include the immunomodulatory disease may be selected from the group consisting of multiple sclerosis, experimental autoimmune encephalomyelitis (both relapsing and remitting), rheumatoid arthritis, anaphylactic hypersensitivity, asthma, allergic rhinitis, atopic dermatitis, vernal conjunctivitis, eczema, urticarial, food allergies, allergic encephalomyelitis, multiple sclerosis, insulin-dependent diabetes mellitus, and autoimmune uveo-retinitis, inflammatory bowel disease, Crohn's disease, regional enteritis, distal ileitis, granulomatous enteritis, regional ileitis, terminal ileitis, ulcerative colitis, autoimmune thyroid disease, hypertension, infectious diseases, *Leishmania major, Mycobacterium leprae, Candida albi-*

*cans, Toxoplasma gondi*, respiratory syncytial virus, human immunodeficiency virus, allograft rejection, graft vs host disease, airway hyper reactivity, atherosclerosis, inflammatory liver disease, and cancer. In a particular aspect, the immunomodulatory disease is selected from allograft rejection (such as graft vs host disease), airway hyper reactivity, atherosclerosis, inflammatory liver disease, and cancer.

Embodiments described herein include administering 1-1000 mg of compound to the patient. The administration may be topical, by inhalation, intranasal, intravenous, intra-articular, intra-arterial, intraperitoneal, intra-thecal, intraventricular, intrasternal, intracranial, intra-muscular or subcutaneous, or by infusion techniques.

Embodiments described herein include a method of antagonizing, inhibiting, decreasing, reducing, suppressing, or disrupting CD1d-mediated, iNKT cell-mediated, and/or iNKT cell TCR-mediated immune signaling comprising administering a composition comprising the compound according to the first or second embodiments described herein. In one aspect, the immune signaling may be triggered by a self-antigen. In a particular aspect of this sixth embodiment, the CD1d-mediated, iNKT cell-mediated, and/or iNKT cell TCR-mediated immune signaling may be the production or inhibition of production of interferon-gamma (IFN-γ), tumor necrosis factor-alpha (TNF-α), IL-1, IL-2, IL-3, IL-4, IL-6, IL-8, IL-10, IL-12, IL-13, IL-16, IL-18 and IL-23, MIP-1a, MIP-113, RANTES, CCL4, CCL5, or GMCSF. In a even more particular aspect, the CD1d-mediated, iNKT cell-mediated, and/or iNKT cell TCR-mediated immune signaling may include the production or inhibition of production of interferon-gamma (IFN-γ), IL-4, or GMCSF.

Embodiments described herein include the use of a therapeutic composition according to the fourth embodiment in the manufacture of a medicament for the treatment of an immunomodulatory condition. Such embodiment also includes a composition as provided according to any of the previous embodiments for use in treating an immunomodulatory condition.

Embodiments described herein include a kit comprising a unit dose of the composition according the first or second embodiments, a container for said unit dose, and an informational package insert.

Embodiments described herein include methods of making the present sphingamide compounds including the particular methods described in Example 1.

Further embodiments and aspects thereof shall be exemplified below, however, it is to be understood that a skilled artisan would recognize how such embodiments may be further modified within the scope of this description to meet the needs of treatments for immune modulated diseases.

BRIEF DESCRIPTION OF THE DRAWINGS

FIG. 5D is a control study, identical to 5(A) but using lipids that lack the amide group, which makes them all agonists. The data show that the amide group prevents iNKT cell activation.

DETAILED DESCRIPTION

Figure 1:
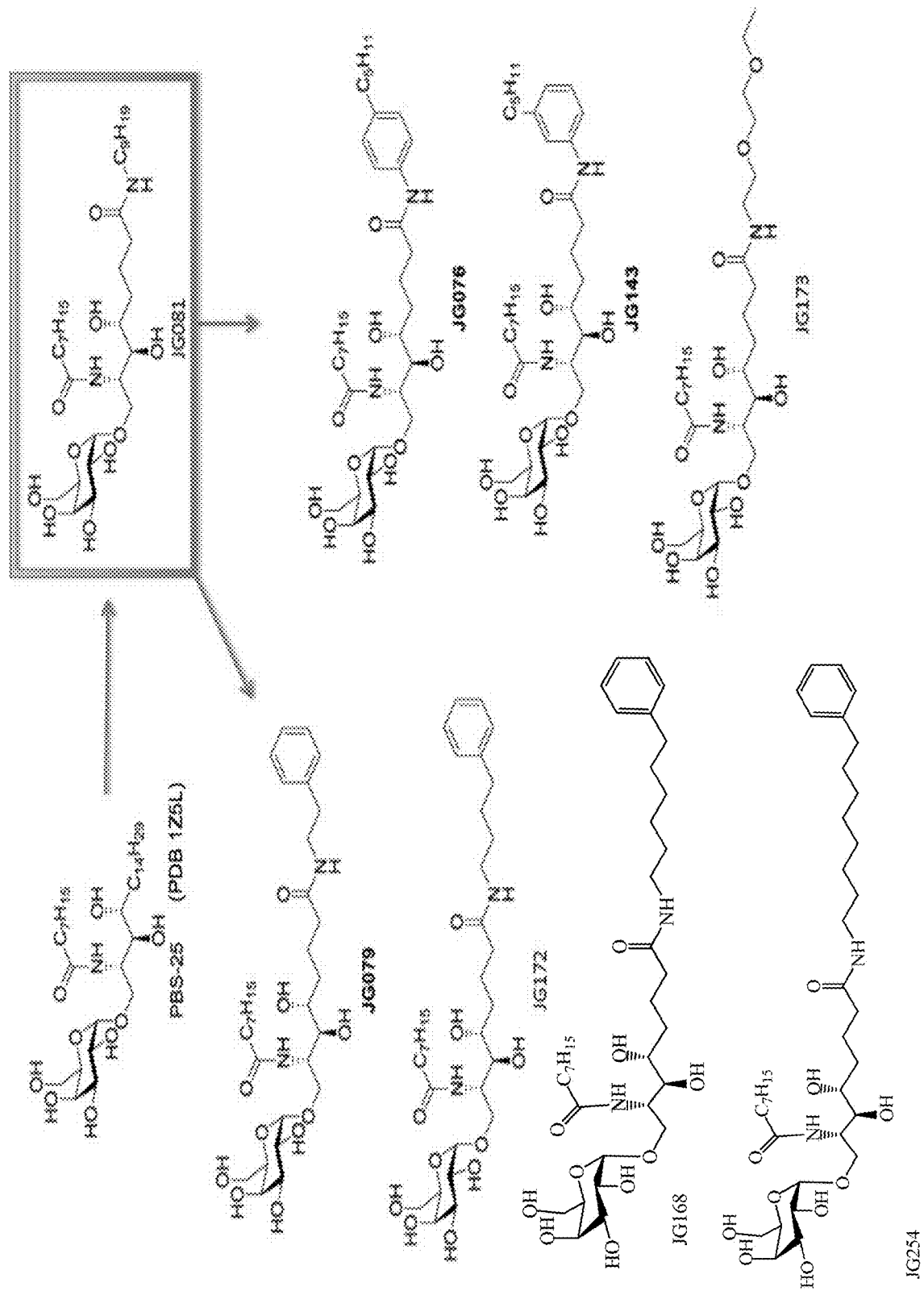
FIG. 1 shows the chemical structures and derivatization of particular examples of the sphingamide compounds described herein.

The compounds, compositions and methods provided herein antagonize, inhibit, decrease, reduce, suppress, or disrupt CD1d-mediated, iNKT cell-mediated, and/or iNKT cell TCR-mediated immune signaling. The sphingamide compounds herein were rationally designed based upon 3D structural considerations in relation to the structures of each of CD1d, the iNKT cell TCR, and the ternary complex CD1d-sphingamide-TCR. More specifically, the addition of an amide in the phytosphingosine tail of a derivative of α-GalCer led to a non-conserved binding with CD1d, a conserved binding with the iNKT cell TCR, and an antagonist-like phenotype. In addition, the solubility of the sphingamide compounds described herein is advantageously improved (e.g., in aqueous solutions) due to the shortened acyl chain lengths in comparison to known agonists, such as α-GalCer, thereby facilitating efficient and effective compound formulation.

Structures

The compounds described herein are sphingamides, including but not limited to compounds of formula I and pharmaceutically acceptable salts thereof:

Formula I

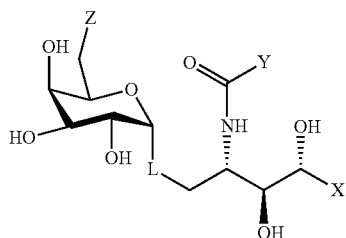

wherein X represents an alkyl chain having 5 to 30 carbons and at least one amide group, wherein the alkyl chain may be substituted by one or more O, S, or P atoms, or a 4 to 6 membered homo- or heterocyclic ring, wherein the heteroatoms, if present, are selected from either O or N and the ring may be substituted with a halogen atom;

wherein Y is an alkyl chain having 5 to 30 carbons and the alkyl chain having 5 to 30 carbons is optionally terminated with a 4 to 6 membered homo- or heterocyclic ring, and the heteroatoms, if present, are selected from either an O or an N atom and the ring may be substituted with a halogen atom;

wherein Z represents a group selected from an —OH, a 2-naphtureido, a phenylureido, a benzyl amide, a 4-pyridinylcarbamoyl, or a 2-napthylcarbamoyl; and, wherein L represents a linker selected from an oxygen atom or a lower alkyl group.

In a particular embodiment of Formula I, X is an alkyl chain having at most 20 carbon atoms and an amide bond. In an embodiment, the X of Formula I is an alkyl chain having at least 6 carbon atoms and at most 20 carbon atoms and an amide bond.

In a particular embodiment, the present compounds include but are not limited to those depicted in Formula II and pharmaceutically acceptable salts thereof:

Formula II

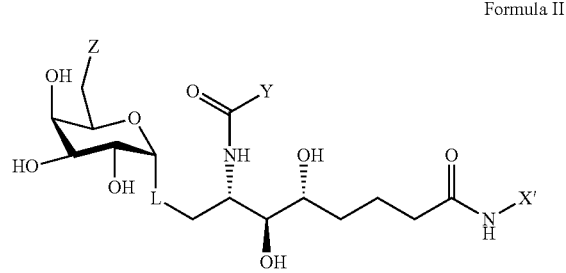

wherein X' is an alkyl chain having two to 8 carbons, one or two carbons optionally substituted with O or a 4 to 6 membered homo- or heterocyclic ring, and the heteroatoms, if present, are selected from either O or N and the ring may be substituted with a halogen atom, wherein the alkyl chain is optionally terminated with a 4 to 6 membered homo- or heterocyclic ring, and the heteroatoms, if present, are selected from either O or N and the ring may be substituted with a halogen atom, wherein Y and Z are described above, and wherein L represents either an oxygen atom or CH$_2$.

In a particular aspect L of either Formula I or Formula II is an oxygen atom.

In a particular aspect of Formula II, X' is selected from:

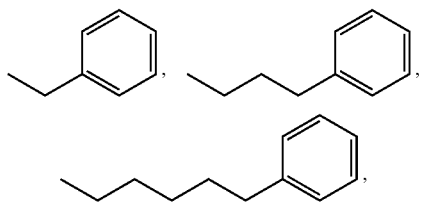

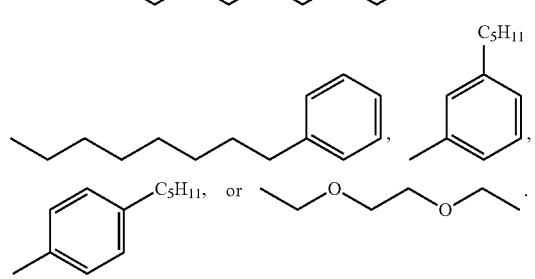

In a particular aspect of either Formula I or Formula II, Y may be selected from: a $C_{27}H_{55}$ unbranched alkyl chain; a $C_{25}H51$ unbranched alkyl chain; a $C_{23}H_{47}$ unbranched alkyl chain; a $C_7H_{15}$ unbranched alkyl chain; or the following structure:

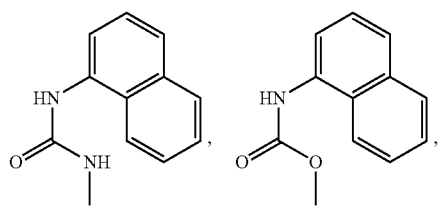

In a particular aspect, Y of either Formula I or Formula II is a $C_7H_{15}$ unbranched alkyl chain.

In a particular aspect of either Formula I or Formula II, Z may be selected from: an —OH group,

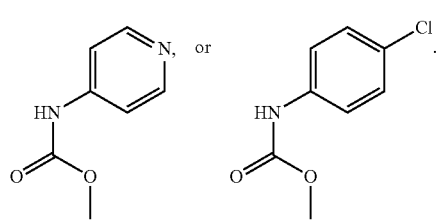

In a specific aspect, Z is an —OH group.

In some embodiments, there are provided compounds comprising formula I, a pharmaceutically acceptable salt thereof, or a prodrug thereof:

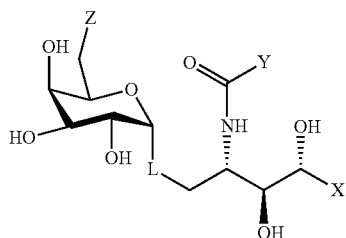

Formula I wherein X represents an alkyl chain having 3 to 30 carbons and having:
  i. at least one intervening amide group and terminating in a phenyl group; or
  ii. a terminating alkyl substituted anilide;
wherein Y is an alkyl chain having 5 to 30 carbons;
wherein Z represents OH; and
wherein L represents an oxygen atom or a C-glycoside analogue thereof.

In some embodiments, there are provided compounds comprising the structure of formula II, a pharmaceutically acceptable salt thereof, or a prodrug thereof:

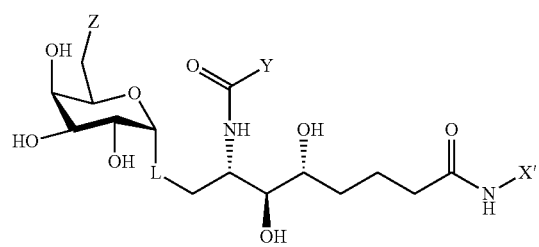

Formula II wherein X' is:
  i. an alkyl chain having two to 8 carbons terminating in a phenyl group; or
  ii. an alkyl substituted phenyl group.

In some embodiments, X' is selected from the group consisting of:

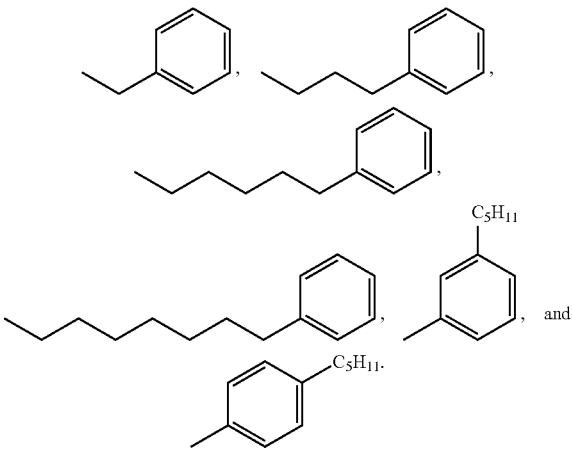

In some embodiments, Y is selected from the group consisting of:
  a $C_{27}H_{55}$ unbranched alkyl chain;
  a $C_{25}H_{51}$ unbranched alkyl chain;
  a $C_{23}H_{47}$ unbranched alkyl chain; and
  a $C_7H_{15}$ unbranched alkyl chain.

In embodiments, the compounds described herein are selected from the following:

JG081

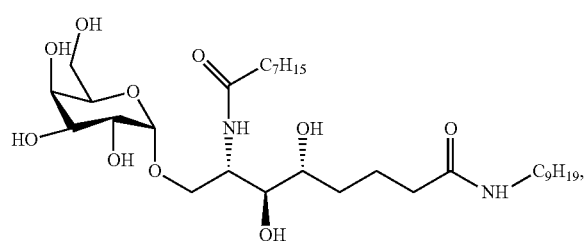

JG079

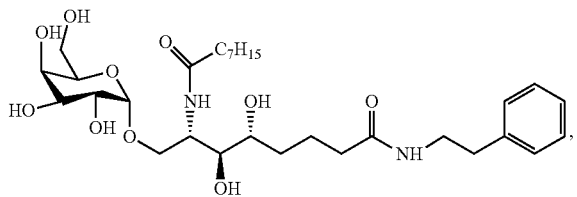

JG172

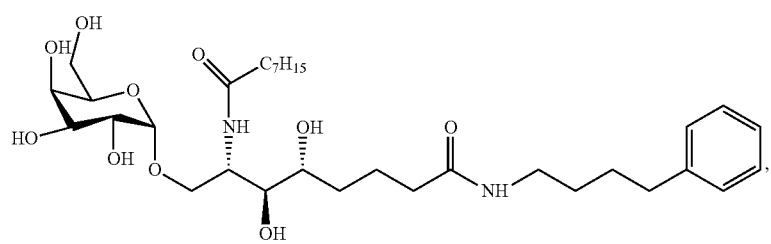

JG168
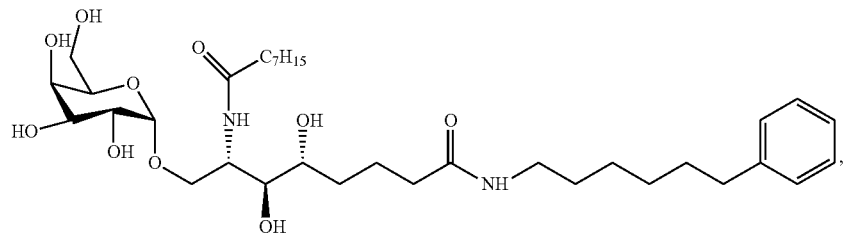
JG254
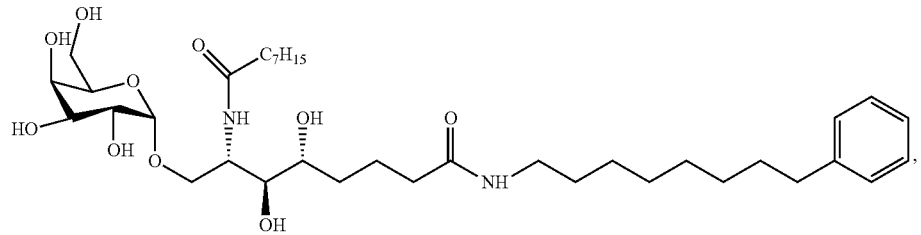
JG076
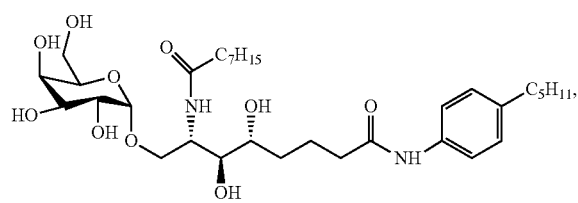
JG143
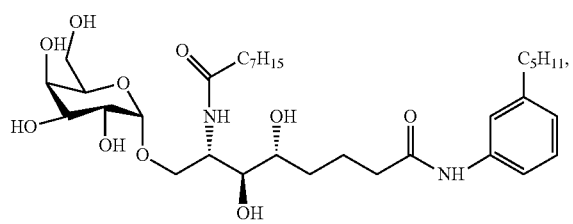
JG173
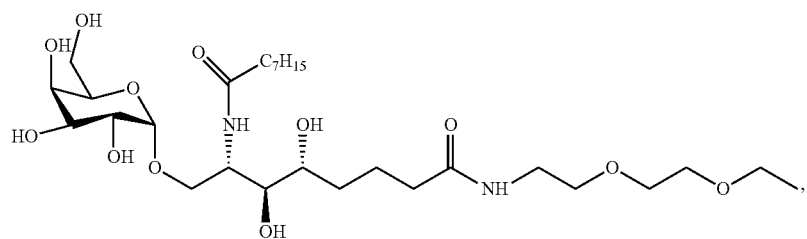
JJ140
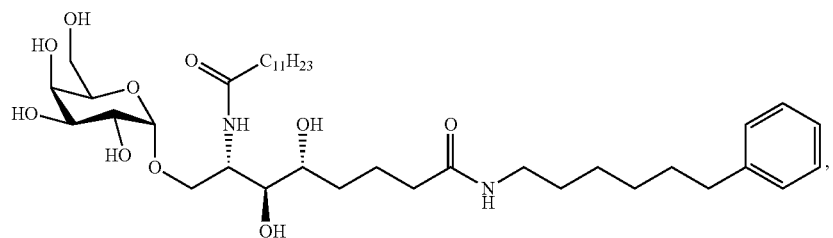
JJ141
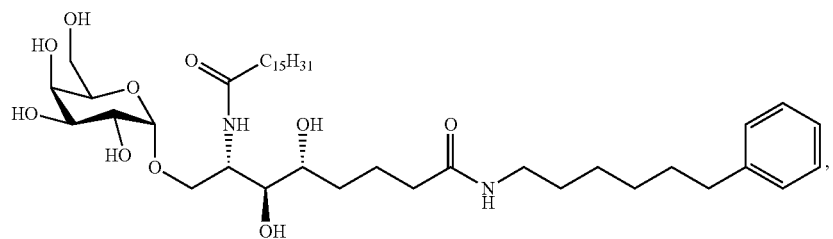

-continued
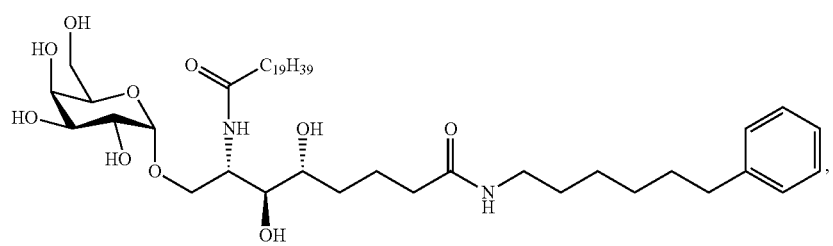
JJ142
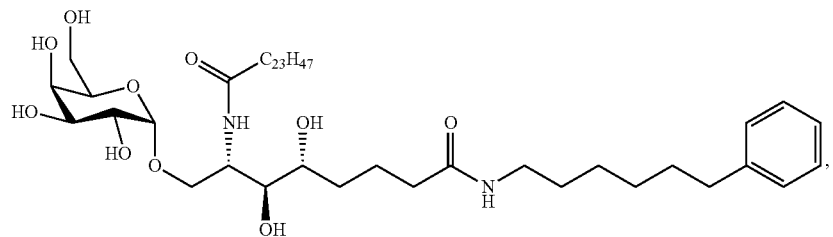
JG293
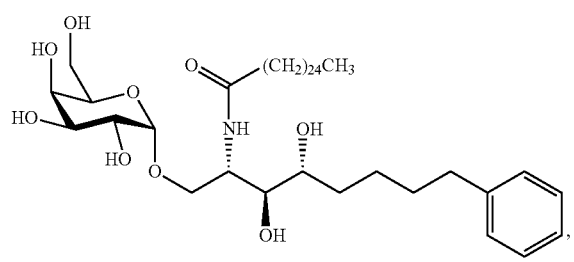
JJ082
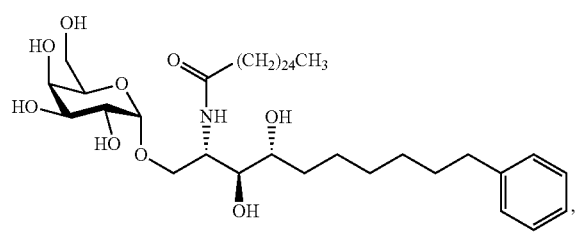
JJ088
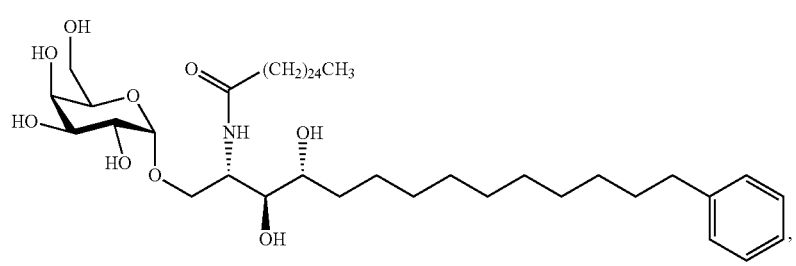
JJ090
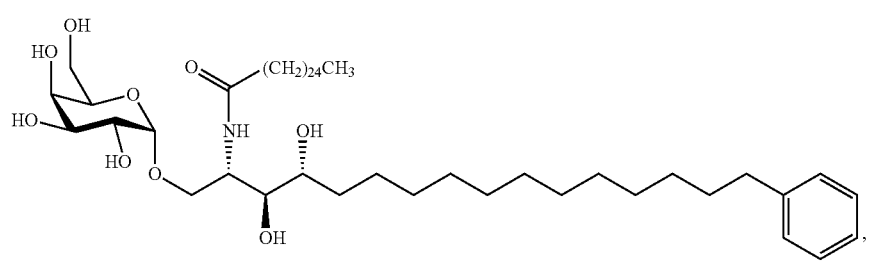
JJ091
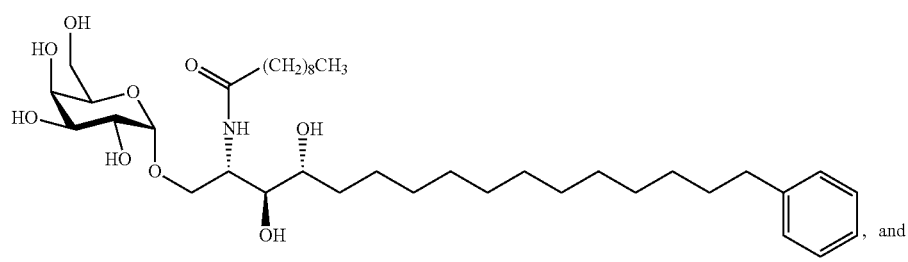
JJ112
(JJ091 with C8 alkyl chain)

JG296

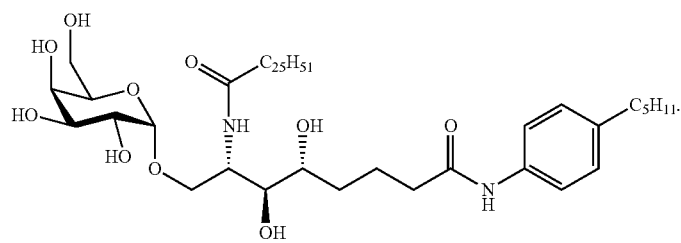

The presently described compounds include their pharmaceutically acceptable salts. The term "salts" includes any anionic and cationic complex, such as the complex formed between a cationic lipid disclosed herein and one or more anions. Non-limiting examples of anions include inorganic and organic anions, e.g., hydride, fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof. In particular embodiments, the salts of the cationic lipids disclosed herein are crystalline salts.

The term "alkyl" includes a straight chain or branched, noncyclic or cyclic, saturated aliphatic hydrocarbon containing from 1 to 30 carbon atoms, 2-28 carbon atoms, 3-28 carbon atoms, 4-28 carbon atoms, 5-28 carbon atoms, 2-27 carbon atoms, 3-27 carbon atoms, 4-27 carbon atoms, 5-27 carbon atoms, 6-27 carbon atoms, 7-27 carbon atoms, 2-25 carbon atoms, 3-25 carbon atoms, 4-25 carbon atoms, 5-25 carbon atoms, etc. Representative saturated straight chain alkyls include, but are not limited to, methyl, ethyl, n-propyl, n-butyl, n-pentyl, n-hexyl, and the like, while saturated branched alkyls include, without limitation, isopropyl, sec-butyl, isobutyl, tert-butyl, isopentyl, and the like. Representative saturated cyclic alkyls include, but are not limited to, cyclopropyl, cyclobutyl, cyclopentyl, cyclohexyl, and the like, while unsaturated cyclic alkyls include, without limitation, cyclopentenyl, cyclohexenyl, and the like. In one aspect, alkyl chains include, but are not limited to straight $C_4$ to $C_{27}$ chains, in particular $C_4$ to $C_{14}$ chains. A lower alkyl is an alkyl having 1 to 6 carbons, and in one aspect 2 to 4 carbons.

The term "alkenyl" includes an alkyl, as defined above, containing at least one double bond between adjacent carbon atoms. Alkenyls include both cis and trans isomers. Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

The term "alkynyl" includes any alkyl or alkenyl, as defined above, which additionally contains at least one triple bond between adjacent carbons. Representative straight chain and branched alkynyls include, without limitation, acetylenyl, propynyl, 1-butynyl, 2-butynyl, 1-pentynyl, 2-pentynyl, 3-methyl-1 butynyl, and the like.

The term "acyl" includes any alkyl, alkenyl, or alkynyl wherein the carbon at the point of attachment is substituted with an oxo group, as defined below. The following are non-limiting examples of acyl groups: —C(=O)alkyl, —C(=O)alkenyl, and —C(=O)alkynyl.

The term "heterocycle" includes a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include, but are not limited to, heteroaryls as defined below, as well as morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" mean that, when substituted, at least one atom is replaced with a substituent. For instance one hydrogen atom may be substituted with a halogen atom. In another example one carbon atom may be substituted with a phenyl ring (a six-membered aromatic ring). In the case of an oxo substituent (=O), two hydrogen atoms are replaced. The term "optionally substituted," when used before a list of substituents means that in a given particular aspect, a substituent may or may not be present.

The term "halogen" includes fluoro, chloro, bromo, and iodo.

The present compounds include prodrugs thereof. As used herein the term "prodrug" refers to a pharmacologically inactive derivative of a parent "drug" molecule that requires biotransformation (e.g., either spontaneous or enzymatic) within the target physiological system to release, or to convert (e.g., enzymatically, mechanically, electromagnetically, etc.) the "prodrug" into the active "drug." "Prodrugs" are designed to overcome problems associated with stability, toxicity, lack of specificity, or limited bioavailability. Exemplary "prodrugs" comprise an active "drug" molecule itself and a chemical masking group (e.g., a group that reversibly suppresses the activity of the "drug"). Some "prodrugs" are variations or derivatives of compounds that have groups cleavable under metabolic conditions. Exemplary "prodrugs" become pharmaceutically active in vivo or in vitro when they undergo solvolysis under physiological conditions or undergo enzymatic degradation or other biochemical transformation (e.g., phosphorylation, hydrogenation, dehydrogenation, glycosylation, etc.). Prodrugs often offer advantages of solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common "prodrugs" include acid derivatives such as esters prepared by reaction of parent acids with a suitable alcohol (e.g., a lower alkanol), amides prepared by reaction of the parent acid compound with an amine (e.g., as described above), or basic groups reacted to form an acylated base derivative (e.g., a lower alkylamide).

As used herein; the term "drug" refers to a pharmacologically active molecule that is used to diagnose, treat, or prevent diseases or pathological conditions in a physiological system (e.g., a subject, or in vivo, in vitro, or ex vivo cells, tissues, and organs). Drugs act by altering the physiology of a living organism, tissue, cell, or in vitro system to which the drug has been administered. It is intended that the terms "drug" and "chemotherapeutic agent" encompass antihyperproliferative and antineoplastic compounds as well as other biologically therapeutic compounds.

Protein Binding

In one embodiment the sphingamide compounds of the present disclosure bind one or more of CD1 or an NKT cell TCR. In a particular aspect, the CD1 is CD1d and the TCR is the iNKT cell TCR.

CD1d is a non-classical MHC I molecule expressed on antigen presenting cells (APCs). Various glycolipids (such as natural microbial glycolipids and certain synthetic glycolipids) bind CD1d and a subset will activate iNKT cells. Broadly, the CD1 family is a glycosylated antigen-presenting molecule on the cell surface of APCs such as DC, M0, and B cells. It is structurally related to MHC class I, but the family is non-polymorphic, with 5 isotypes (CD1a-e). CD1 overall resembles MHC I molecules, where the heavy chain (MHC or CD1) non-covalently associates with β2-microglobulin (β2m). The heavy chain can further be divided into three domains. The N-terminal α1 and α2 domains together form the antigen-binding site, while the α3-domain pairs with β2m to support the α1-2 platform. The CD1 binding groove is formed by two anti-parallel α-helices that sit atop an anti-parallel β-sheet platform. CD1d in particular has evolved a hydrophobic antigen-binding groove, which is deeper than that of MHC I and well suited for the binding and presentation of hydrophobic molecules, such as lipids. For in-depth information about the structural details of different CD1 isoforms and species, see Zeng et al., Science (1997) 277:339-45.10.1126/science.277.5324.339; Garcia-Alles et al., Proc Natl Acad Sci USA (2011) 108:13230-5.10.1073/pnas.1105627108; Wang et al., PLoS One (2012) 7:e47989.10.1371/journal.pone.0047989.

In one aspect, the sphingamide compounds described herein bind to a mammalian Cd1d, such as a CD1d from human, mouse, rat, guinea pig, cow, monkey, rabbit, hamster or others.

Mice have two CD1d genes. CD1d1 and CD1d2 have a high homo-logy as understood in the art. For use herein, CD1d1 is referenced. An example of mouse CD1d1 may be found under UniProt sequence P11609-1, with a 17 amino acid signal sequence and a start codon.

>sp|P11609|CD1D1_MOUSE Antigen-presenting glycoprotein CD1d1 OS = Mus musculus GN = Cd1d1 PE = 1 SV = 3

(SEQ ID NO: 1)
MRYLPWLLLLWAFLQVWGQSEAQQKNYTFRCLQMSSFANRSWSRTDSVVWL

GDLQTHRWSNDSATISFTKPWSQGKLSNQQWEKLQHMFQVYRVSFTRDIQ

ELVKMMSPKEDYPIEIQLSAGCEMYPGNASESFLHVAFQGKYVVRFWGTS

WQTVPGAPSWLDLPIKVLNADQGTSATVQMLLNDTCPLFVRGLLEAGKSD

LEKQEKPVAWLSSVPSSADGHRQLVCHVSGFYPKPVWVMWMRGDQEQQGT

HRGDFLPNADETWYLQATLDVEAGEEAGLACRVKHSSLGGQDIILYWDAR

QAPVGLIVFIVLIMLVVVGAVVYYIWRRRSAYQDIR

Unless otherwise indicated, references to amino acid residues are made to amino acid positions of the processed protein, i.e., without the start codon or signal sequence. Thus, many references are made to SEQ ID NO: 2, as shown below:

(SEQ ID NO: 2)
SEAQQKNYTFRCLQMSSFANRSWSRTDSVVWLGDLQTHRWSNDSATISFT

KPWSQGKLSNQQWEKLQHMFQVYRVSFTRDIQELVKMMSPKEDYPIEIQL

SAGCEMYPGNASESFLHVAFQGKYVVRFWGTSWQTVPGAPSWLDLPIKVL

NADQGTSATVQMLLNDTCPLFVRGLLEAGKSDLEKQEKPVAWLSSVPSSA

DGHRQLVCHVSGFYPKPVWVMWMRGDQEQQGTHRGDFLPNADETWYLQAT

LDVEAGEEAGLACRVKHSSLGGQDIILYWDARQAPVGLIVFIVLIMLVVV

GAVVYYIWRRRSAYQDIR

A reference human CD1d sequence may be Uniprot 15813, having a start codon and a 19 amino acid signal sequence.

>sp|P15813|CD1D_HUMAN Antigen-presenting glycoprotein CD1d OS = Homo-sapiens GN = CD1D PE = 1 SV = 1

(SEQ ID NO: 3)
MGCLLFLLLWALLQAWGSAEVPQRLFPLRCLQISSFANSSWTRTDGLAWL

GELQTHSWSNDSDTVRSLKPWSQGTFSDQQWETLQHIFRVYRSSFTRDVK

EFAKMLRLSYPLELQVSAGCEVHPGNASNNFFHVAFQGKDILSFQGTSWE

PTQEAPLWVNLAIQVLNQDKWTRETVQWLLNGTCPQFVSGLLESGKSELK

KQVKPKAWLSRGPSPGPGRLLLVCHVSGFYPKPVWVKWMRGEQEQQGTQP

GDILPNADETWYLRATLDVVAGEAAGLSCRVKHSSLEGQDIVLYWGGSYT

SMGLIALAVLACLLFLLIVGFTSRFKRQTSYQGVL

Unless otherwise indicated, references to amino acid residues are made to amino acid positions of the processed protein, i.e., without the start codon or signal sequence. Thus, many references are made to SEQ ID NO: 4, as shown below:

(SEQ ID NO: 4)
VPQRLFPLRCLQISSFANSSWTRTDGLAWLGELQTHSWSNDSDTVRSLKP

WSQGTFSDQQWETLQHIFRVYRSSFTRDVKEFAKMLRLSYPLELQVSAGC

EVHPGNASNNFFHVAFQGKDILSFQGTSWEPTQEAPLWVNLAIQVLNQDK

WTRETVQWLLNGTCPQFVSGLLESGKSELKKQVKPKAWLSRGPSPGPGRL

LLVCHVSGFYPKPVWVKWMRGEQEQQGTQPGDILPNADETWYLRATLDVV

AGEAAGLSCRVKHSSLEGQDIVLYWGGSYTSMGLIALAVLACLLFLLIVG

FTSRFKRQTSYQGVL iNKT-Cell Receptor (TCR)—

In one embodiment, the present sphingamide compounds bind an iNKT cell TCR. In one aspect, the iNKT cell TCR is a TCR from a mammal, such as a human, mouse, rat, guinea pig, cow, monkey, rabbit, hamster or others.

iNKT express a heterodimeric TCR antigen receptor having an α and β chain. The iNKT cell TCR is semi-invariant as it contains a conserved Vα14 chain in mice and Vα24 chain in human that both re-arrange with Jα18, while the Vβchain is more variable. It is proposed that only germline encoded residues are important for the recognition of a glycolipid. In one aspect, the present sphingamide compounds bind TCRs including but not limited to: the Vα14Vβ8.2 TCR, Vα14Vβ7 TCR, and Vα14Vβ10 TCR. Hybridomas secreting these TCRs include the Murine iNKT hybridomas DN3A4-1.2 (Vα14Vβ8.2), DN3A4-1.4 (Vα14Vβ10), N38.2H4 (Vα14Vβ7) and DN32.D3 (Vα14Vβ8.2).

Sequences for multiple α and β chains of various TCRs are listed below. Notably, the structures are closely related. For instance the α chain of mouse Vα14Jα18 (GenBank: AAA40180.1) is SEQ ID NO: 5

(SEQ ID NO: 5)
MKKRLSACWVVLWLHYQWVAGKTQVEQSPQSLVVRQGENCVLQCNYSVTP

DNHLRWFKQDTGKGLVSLTVLVDQKDKTSNGRYSATLDKDAKHSTLHITA

TLLDDTATYICVVGDRGSALGRLHFGAGTQLIVIPDIQNPEPAVYQLKDP

RSQDSTLCLFTDFDSQINVPKTMESGTFITDKTVLDMKAMDSKSNGAIAW

SNQTSFTCQDIFKETNATYPSSDVPCDATLTEKSFETDMNLNFQNLSVMG

LRILLLKVAGFNLLMTLRLWSS

The β chain of mouse Vβ8.2 (Genbank ABC69269.1) has the sequence SEQ ID NO: 6:

(SEQ ID NO: 6)
MGSRLFFVLSSLLCSKHMEAAVTQSPRNKVAVTGGKVTLSCNQTNNHNNM

YWYRQDTGHGLRLIHYSYGAGSTEKGDIPDGYKASRPSQENFSLILELAT

PSQTSVYFCASGEGGLGGPTQYFGPGTRLLVLEDLRNVTPPKVSLFEPSK

AEIANKQKATLVCLARGFFPDHVELSWWVNGKEVHSGVSTDPQAYKESNY

SYCLSSRLRVSATFWHNPRNHFRCQVQFHGLSEEDKWPEGSPKPVTQNIS

AEAWGRADCGITSASYHQGVLSATILYEILLGKATLYAVLVSGLVLRPGQ

EKNS

The β chain of mouse Vβ7 has the sequence shown in SEQ ID NO: 7. Notably this sequence is similar to Genbank: AAB16802.1 but with different CDR3β:

(SEQ ID NO: 7)
MRVRLISAVVLCFLGTGLVDMKVTQMPRYLIKRMGENVLLECGQDMSHET

MYWYRQDPGLGLQLIYISYDVDSNSEGDIPKGYRVSRKKREHFSLILDSA

KTNQTSVYFCASSLRGQNTLYFGAGTRLSVLEDLRNVTPPKVSLFEPSKA

EIANKQKATLVCLARGFFPDHVELSWWVNGKEVHSGVSTDPQAYKESNYS

YCLSSRLRVSATFWHNPRNHFRCQVQFHGLSEEDKWPEGSPKPVTQNISA

EAWGRADCGITSASYHQGVLSATILYEILLGKGHPICCAQWPSADEG

The β chain of mouse Vβ2 has the sequence shown in SEQ ID NO: 8, and is similar to Genbank: AGH62473.1 but with different CDR3β. Also the start codon (amino add M) is missing from SEQ ID NO: 8 and would be added if this were to be expressed:

(SEQ ID NO: 8)
LLEQNPRWRLVPRGQAVNLRCILKNSQYPWMSWYQQDLQKQLQWLFTLRS

PGDKEVKSLPGADYLATRVTDTELRLQVANMSQGRTLYCTCSARLGDNQD

TQYFGPGTRLLVLEDLRNV

The α chain of human Vα24Jα18 (Genbank ABC72374.1) has the following sequence (SEC) ID NO: 9)

(SEQ ID NO: 9)
MKKHLTTFLVILWLYFYRGNGKNQVEQSPQSLIILEGKNCTLQCNYTVSP

FSNLRWYKQDTGRGPVSLTIMTFSENTKSNGRYTATLDADTKQSSLHITA

SQLSDSASYICVVSDRGSTLGRLYFGRGTQLTVWPDIQNPDPAVYQLRDS

KSSDKSVCLFTDFDSQTNVSQSKDSDVTITDKTVLDMRSMDFKSNSAVAW

SNKSDFACANAFNNSIIPEDTFFPSPESSCDVKLVEKSFETDTNLNFQNL

SVIGFRILLLKVAGFNLLMTLRLWSS

The β chain of human Vβ11 has a sequence shown in SEQ ID NO: 10, and is similar to Genbank ABC72386.1 but with different CDR3b.

(SEQ ID NO: 10)
MSTRLLCYVGFYFLGAGLMEADIYQTPRYLVIGTGKKITLECSQTMGHDK

MYWYQQDPGMELELIHYSYGVNSTEKGDLSSESTVSRIRTEHFPLTLESA

RPSHTSQYLCASSAKDRQVSSQETQYFGPGTRLLVLEDLKNVFPPEVAVF

EPSEAEISHTQKATLVCLATGFYPDHVELSWWVNGKEVESGVSTDPQPLK

EQPALNDSRYCLSSRLRVSATFWQPRNHFRCQVVQFYGLSENDEWTQDRA

KPVTQIVSAEAWGRADCGFTSVSYQQGVLSATILYEILLGKATLYAVLVS

ALVLMAMVKRKDF

The present compounds may bind any of the proteins described herein or a protein having substantial identity thereto. As applied to polypeptides, the term "substantial identity" means that two peptide sequences, when optimally aligned, such as by the programs GAP or BESTFIT using default gap weights, share at least 80 percent sequence identity, at least 85 percent sequence identity, at least 90 percent sequence identity, at least 95 percent sequence identity or more (e.g., 97 percent sequence identity or 99 percent sequence identity). Residue positions that are not identical may differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Some conservative amino acids substitution groups are: valine-leucine-isoleucine, phenylalanine-tyrosine, lysine-arginine, alanine-valine, and asparagine-glutamine. For instance, there is a substantial identity between various CDR3α peptide sequences from differing iNKT clones. In one aspect, amino acid sequences are substantially identical if they have at most 10, 9, 8, 7, 6, 5, 4, 3, 2, or 1 amino acid substitutions. In a further aspect, amino acid sequences are substantially identical if they have at most 10, 9, 8, 7, 6, 5, 4, 3, 2, or 1 conservative amino acid substitutions.

The present compounds may bind a fragment of a protein described herein. The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are 20 amino acids long, usually at least 50 amino acids long or longer, and span the portion of the polypeptide required for intermolecular binding of the compositions disclosed herein with its various ligands and/or substrates. For instance, fragments include the complementarity determining regions (CDR) of the TCR (e.g., CDR 1-3 of the α or β chain of the TCR), or the α1 chain of CD1d or the α2 chain of CD1d. In one particular aspect, the present compounds may bind to a CDR3α fragment of the iNKT TCR.

Binding Level Description

In one embodiment the sphingamide compounds of the present disclosure bind a CD1 in a non-conserved manner when compared to the binding of α-GalCer or another native lipid such as GalA-GSL, the diacyl glycerols from B. Burgdoferi, Glc-DAG-s2, or Agelasphin 9b. Each CD1 protein has adopted isoform and species-specific binding pockets that differ in shape and size; however, all mammalian CD1 binding grooves contain the two major pockets, A' and F'. While the A' pocket is larger, donut shaped, and deeply buried, the F' pocket is more open and accessible to the solvent. In CD1d, each hydrophobic pocket generally binds one alkyl chain of a dual alkyl chain glycolipid, while the carbohydrate portion is located at the CD1d surface for TCR interaction. TCR recognition requires the proper presentation of the glycolipids by CD1d and TCR binding of the exposed carbohydrate epitope in conjunction with CD1d. The lipid backbone itself can also be in contact with the TCR to varying degrees; however, CD1d's main role is to anchor and orient the carbohydrate for T cell recognition. While the CD1d binding groove is fairly rigid, however, the binding groove accommodates different lipids showing flexibility especially at the surfaces above both A' and F' pockets where subtle structural changes can be induced upon lipid and/or TCR binding. Lipid-induced structural changes in mouse CD1d have only been observed by using synthetic glycolipids and whether natural lipids exist that have the same effect is currently unknown. However, lipid-induced structural changes especially around the F' pocket greatly influence iNKT cell activation as this is the primary binding site for the TCR.

Particular amino acid residues of interest when binding mouse CD1d include D153, T156, T159, D80, R79, Y73, F77, or W133 of SEQ ID NO: 2 (mouse CD1d without its signal sequence). α-GalCer creates hydrogen bonds with D80, D153, T156 and T159 (see Aspeslagh et al., 2011 EMBO J., 30:2294-2305, the entire contents of which are hereby incorporated by reference). In one embodiment, the present compounds bind differently, creating hydrogen bonds with D80 and D153, but not with T156 or T159. Another particular aspect is that the sphingamide compounds of the present disclosure may form an additional hydrogen bond with mCD1d at Y73, when the sphingamide compound is also bound by the iNKT cell TCR (i.e., is in the ternary complex).

In one embodiment, the present sphingamide compounds bind the iNKT cell TCR in the same manner as α-GalCer (i.e., binding is conserved). Particular amino acid residues in the mouse Vα14Vβ8.2 iNKT cell TCR associated with binding are N30, G96, and R95 of SEQ ID NO: 6 (see Aspeslagh, 2011 EMBO J., 30:2294-2305). In one embodiment, like α-GalCer, the present compounds create hydrogen bonds with N30 and G96.

Similarly, the present sphingamide compounds may bind the human Vα24Vβ11 TCR, e.g., SEQ ID NO: 10 in the same manner as α-GalCer. Particular amino acid residues in the human Vα24Vβ11 TCR associated with binding are R95, G96, S30, and F29 of SEQ ID NO: 10.

In one embodiment, the compounds described herein bind CD1d with less affinity than α-GalCer binds CD1d. As used herein "avidity" means the accumulated strength of multiple affinities of individual non-covalent binding interactions, such as between a protein receptor and its ligand, and is commonly referred to as functional affinity. The binding affinity is also measured, which is a measure of dynamic equilibrium of the ratio of on-rate ($k_a$) and off-rate ($k_d$) under specific concentrations of reactants. In one embodiment, the present sphingamide compounds bind CD1d and/or iNKT cell receptor with a $K_D$ in the micromolar to nanomolar range. In one embodiment, the present sphingamide compounds bind CD1d and/or iNKT cell receptor with a $K_D$ of lower than about 10 micromolar, lower than about 1 micromolar, lower than about 0.5 micromolar, lower than about 0.25 micromolar, lower than about 0.1 micromolar, lower than about 75 nanomolar, lower than about 50 nanomolar, lower than about 25 nanomolar, lower than about 20 nanomolar, lower than about 15 nanomolar, or lower than about 10 nanomolar. In a particular aspect, the mouse TCR will bind the present sphingamide compounds with a $K_D$ of about 100-500 nanomolar. In a further aspect, the present sphingamide compounds bind a human TCR with a $K_D$ of about 1-5 micromolar.

The term "naturally occurring" or "native" when used in connection with biological materials such as nucleic acid molecules, polypeptides, host cells, lipids and the like, refers to those which are found in nature and not manipulated by a human being.

Agonist/Antagonist

In one embodiment, the present compounds may have an agonist activity. An agonist, as used herein, is a mimetic of the natural ligand and produces a similar biological effect as the natural ligand when it binds to the receptor. It binds at the same binding site, and leads, in the absence of the natural ligand, to either a full or partial response. In the latter case, it is called a partial agonist. An example of a CD1d or iNKT cell T cell agonist is α-GalCer.

In another embodiment, the present compounds may have an inverse agonist activity. As used herein, the term "inverse agonist" is a ligand which when bound to its receptor, decreases or inhibits the receptor's basal activity. If either the natural ligand or an agonist binds to the receptor site, the basal activity is increased. If however, an inverse agonist binds, the activity is decreased.

In yet another embodiment, the present compounds have an antagonist activity. Antagonist is defined broadly and is used to mean a ligand which decreases the effects of an agonist. These may be immediate effects or downstream effects. An antagonist may be a competitive antagonist, which interferes with the binding of the agonist with its receptor, or a non-competitive agonist, which binds at a different location than the agonist. Competitive binding may be determined by methods well known to those skilled in the art such as ELISA, immunohistochemistry, immunoprecipitation, Western blots, radiolabelling experiments and other methods known in the art. In one embodiment, the present compounds are competitive antagonists of longer lipids and weaker CD1d-binding self antigens that cause CD1d-mediated, iNKT cell-mediated, and/or iNK T-cell receptor-mediated immune signaling.

Further, the compounds described herein may be partial antagonists, and display a decrease in some of the effects expected of an agonist while maintaining or even increasing other effects. For example several studies suggest that phophtidylethanolamine and liposomes can bind CD1d and inhibit, decrease, antagonize, reduce, suppress, or prevent iNKT activation. In addition di-palmitoyl-phosphatidyl-ethanolamine (DPPE) covalently attached to polyethyleglycol (PEG) has been shown to be a CD1-dependent antagonist (see Lombardi et al., J. Immunol. 2010, 184(4):2107-2115, the entire contents of which are hereby incorporated by reference).

In one aspect, the present sphingamide compounds have an inhibitory or disruptive activity. As used herein the terms inhibit, decrease, reduce, suppress, or disrupt are all used to indicate that the CD1d-mediated, iNKT cell-mediated, and/or iNK T-cell receptor-mediated immune signaling is decreased or stopped. The compounds described herein act by inhibiting or otherwise decreasing the activation and/or cell signaling pathways of the cell expressing either CD1d or the iNK T-cell receptor.

Furthermore, the compounds described herein may inhibit immune responses triggered by other immunological mechanisms. That is, if a bystander cell is stimulated to produce IFN-γ by the introduction of a peptide antigen, the administration of the present compounds may work through the CD1d/iNKT pathway to provide an inhibitory signal to decrease IFN-γ production by the iNKT cell or bystander cell. Similarly, if ovalbumin is administered to mice, a Th2 response may be triggered in other cells, yet administration of the present compounds may inhibit iNKT production of IL-4 and IFN-γ. In one particular embodiment, the present sphingamide compounds described herein inhibit, decrease, antagonize, reduce, suppress, or prevent an immune response triggered or stimulated by a self-antigen.

Immune Response

Embodiments herein provide compositions for modifying or altering (i.e., increasing or decreasing in a statistically significant manner, for example, relative to an appropriate control as will be familiar to persons skilled in the art) immune responses or immune signaling in a host capable of mounting an immune response or conveying immunological signals. As will be known to persons having ordinary skill in the art, an immune response may be any active alteration of the immune status of a host, which may include any alteration in the structure or function of one or more tissues, organs, cells or molecules that participate in maintenance and/or regulation of host immune status. Typically, immune responses may be detected by any of a variety of well-known parameters, including but not limited to in vivo or in vitro determination of: soluble immunoglobulins or antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death); or any other criterion by which the presence of an immune response may be detected.

Immune responses may often be regarded, for instance, as discrimination between self and non-self structures by the cells and tissues of a host's immune system at the molecular and cellular levels, but embodiments herein should not be so limited. For example, immune responses may also include immune system state changes that result from immune recognition of self molecules, cells or tissues, as may accompany any number of normal conditions such as typical regulation of immune system components, or as may be present in pathological conditions such as the inappropriate autoimmune responses observed in autoimmune and degenerative diseases. As another example, in addition to induction by upregulation of particular immune system activities (such as antibody and/or cytokine production, or activation of cell mediated immunity) immune responses may also include suppression, attenuation or any other down-regulation of detectable immunity, which may be the consequence of the antigen selected, the route of antigen administration, specific tolerance induction or other factors. Thus, in one particular embodiment, the present sphingamide compounds inhibit, decrease, antagonize, reduce, suppress, or prevent an immune response caused by a self antigen. In a particular aspect, the self antigen has a lower avidity for CD1d, the iNKT cell TCR, or the ternary complex than the sphingamide compound described herein does.

Determination of the induction or suppression of an immune response by the sphingamide compounds described herein may be established by any of a number of well-known immunological assays with which those having ordinary skill in the art will be readily familiar. Such assays frequently determine immune signaling by detecting in vivo or in vitro determination of: soluble antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death). Procedures for performing these and similar assays are widely known and may be found, for example in Lefkovits (Immunology Methods Manual: The Comprehensive Sourcebook of Techniques, 1998; see also Current Protocols in Immunology; see also, e.g., Weir, Handbook of Experimental Immunology, 1986 Blackwell Scientific, Boston, Mass.; Mishell and Shigii (eds.) Selected Methods in Cellular Immunology, 1979 Freeman Publishing, San Francisco, Calif.; Green and Reed, 1998 Science 281:1309 and references cited therein).

A signal is "mediated" by a protein or other cell function when modification of the protein or function modifies the immune signal. For instance, iNKT-mediated signaling may be modified by interfering with CD1d binding or loading, iNKT cell TCR binding, an abrogation of the function of the iNKT cell TCR, or interference with the iNKT cell cytokine production or secretion.

Any number of other immunological parameters may be monitored using routine assays that are well known in the art.

In certain embodiments the immune response may comprise at least one of production or inhibition of the production of one or a plurality of cytokines wherein the cytokine is selected from interferon-gamma (IFN-γ), tumor necrosis factor-alpha (TNF-α), production of one or a plurality of interleukins wherein the interleukin is selected from IL-1, IL-2, IL-3, IL-4, IL-6, IL-8, IL-10, IL-12, IL-13, IL-16, IL-18 and IL-23, production or inhibition of the production of one or a plurality of chemokines wherein the chemokine is selected from MIP-1a, MIP-1l3, RANTES, CCL4 and CCL5, and a lymphocyte response that is selected from a memory T cell response, a memory B cell response, an effector T cell response, a cytotoxic T cell response and an effector B cell response. In particular embodiments, the present sphingamide compounds decrease the production of IL-2 by iNKT cells in comparison to the amount of IL-2 produced when the iNKT cells bind PBS-25. Further, in a particular aspect the present sphingamide compounds decrease the production of IFN-γ or IL-4 in comparison to the amount of IFN-γ or IL-4 produced when the iNKT cells bind α-GalCer.

By "decrease," "decreasing," "reduce," or "reducing" of an immune response is intended to mean a detectable decrease of an immune response that is the result of the administration of a given antagonist. For instance, the amount of decrease of an immune response by an sphingamide compound described herein may be determined relative to the level of an immune response without administration of the spingamide compound, or as determined relative to the level of an immune response after administration of a Th1 or Th2 polarizing CD1d agonist, iNKT cell activator, or iNKT-cell receptor (TCR) agonist (for example, after the administration of α-GalCer). A detectable decrease can be about 5%, 10%, 15%, 20%, 25%, 30%, 35%, 40%, 45%, 50%, 55%, 60%, 65%, 70%, 75%, 80%, 85%, 90%, 95%, 100%, or more lower than the immune response detected in the absence of the administration of the antagonist. A detectable decrease can be about 5%, 10%, 15%, 20%, 25%, 30%, 35%, 40%, 45%, 50%, 55%, 60%, 65%, 70%, 75%, 80%, 85%, 90%, 95%, or at least about 100% lower than the immune response detected after administration of a Th1 or Th2 polarizing CD1d agonist, iNKT cell activator, or iNKT cell TCR agonist. A decrease in the immune response to the antagonist is typically measured by a decrease in cytokine production (e.g., IFNγ, IFNα, TNFα, IL-6, IL-8, or IL-12) by the binding cell or a responder (bystander) cell in vitro or a decrease in cytokine production in the sera of a mammalian subject after administration of the antagonist.

Control Ligands of Interest and their Binding

The present sphingamide compounds show different chemical and biological characteristics than compounds known in the art. In particular, the binding of the present sphingamide compounds differs from the binding of α-GalCer, OCH, and PBS-25.

α-Galactosylceramide (α-GalCer, N-[(2S,3S,4R)-3,4-Dihydroxy-1-[(2S,3R,4S,5R,6R)-3,4,5-trihydroxy-6-(hydroxymethyl)oxan-2-yl]oxyoctadecan-2-yl]hexacosanamide) has the following structure:

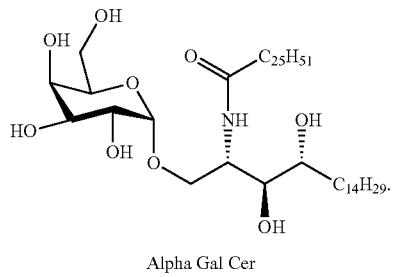

Alpha Gal Cer

α-GalCer consists of a galactose head group that is α-anomerically linked to a phytoceramide, which is composed of a phytosphingosine chain coupled to an acyl chain (fatty acid chain). The crystal structures of both mouse and human CD1d bound to α-GalCer show that both alkyl chains fit into two pockets of CD1d, the sphingoid base chain in the F' pocket and the C26 acyl chain in the A' pocket, while the galactose is exposed at the CD1d surface for interaction with the TCR (Koch et al, 2005; Zajonc et al, 2005a). When α-GalCer is bound to mouse CD1d it forms hydrogen bonds to D153, T156, T159, and D80. Other important residues for binding include Arg79. The invariant α chain of the TCR recognizes the sugar moiety, whereas the TCR-β chain interacts with CD1d residues. However, in contrast to conventional T cells, the complementarity determining regions of the iNKT TCR do not alter their conformation upon antigen recognition (Borg et al, 2007) and appear to be functionally conserved in both mouse and man (Pellicci et al, 2009). When α-GalCer is bound to the mouse TCR Vα14Vβ8.2, it forms hydrogen bonds with the N30, R95 and G96 residues of the TCR. The affinity of CD1d-α-GalCer for the semi-invariant Vα14 T cell receptor is in the low nanomolar range (about 30 to 90 nM).

Administration of α-GalCer in mice activates iNKT cells, generating a primarily TH1 (pro-inflammatory) response. Further research has been conducted to discover other compounds which produce a polarized Th1 or Th2 response.

OCH is an analog of α-GalCer having the following structure:

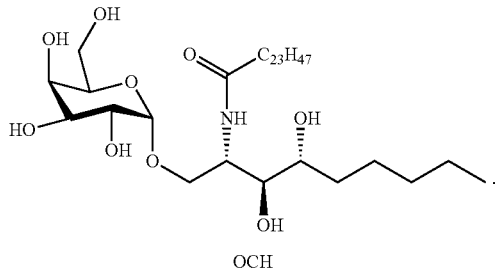

OCH

Th2-biasing OCH has a lower TCR avidity than α-GalCer. Notably OCH has a shorter lipid tail (C24:0) than α-GalCer, and it has been hypothesized that this shorter tail length has biased the cytokine release profile towards a Th2 response (Trappeniers et al., 2008, J. Am. Chem. Soc.) by preventing the formation of the F' roof when bound to CD1d within the F'-pocket (Aspeslagh et al., J. Immunol. 2013, 191(6), the entire contents of which are hereby expressly incorporated by reference). Although the CD1d-exposed portions of OCH and α-GalCer are identical, structural analysis indicates that there are subtle CD1d conformational differences due to differences in the buried lipid portion of these two antigens, likely accounting for the difference in antigenic potency. (Sullivan et al., J Immunol. 2010 Jan. 1; 184(1): 141-153). OCH induces stronger interleukin-4 (IL-4) secretion and weaker interferon-γ (IFN-γ) secretion than α-GalCer both in vitro and in vivo and can inhibit, decrease, antagonize, reduce, suppress, or prevent experimental autoimmune encephalitis in mice. OCH is known for weakly binding the iNKT cell TCR. (Oki et al., J. Clin. Invest. 2004; 113:1631-1640). A further "spacer lipid" may also itself into the F' pocket of the CD1d in the cavity normally occupied by a longer alkyl chain; further stabilizing the binding of OCH.

PBS-25, as shown in the following structure, has an eight carbonyl acyl chain instead of the long C26 fatty acid chain of the original α-GalCer.

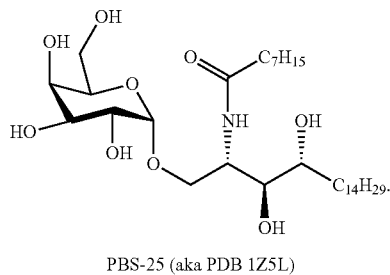

PBS-25 (aka PDB 1Z5L)

Other than the chain length, the phytosphingosine and α-galactose moieties of PBS-25 are similar to their counterparts in α-GalCer. When loaded onto plate-bound CD1d, PBS-25 was as potent as α-GalCer in stimulating both mouse and human iNKT cells. CD1d tetramers loaded with either α-GalCer or PBS-25 also showed similar staining profiles when tested on Vα14 NKT hybridomas, murine NKT cells (blood, spleen and liver) and a human line. Thus, like α-GalCer, PBS-25 loads onto murine and human CD1d and binds the whole population of canonical Vα14 or Vα24 NKT cells (see Zajonc et al., Nat Immunol. 2005 August; 6(8): 810-818, the entire contents of which are hereby incorporated by reference). Importantly, PBS-25, like all other variants of α-GalCer with shorter fatty acid chains, exhibits an accentuated Th2 profile as compared to α-GalCer. Unlike α-GalCer or OCH, which are poorly soluble and require either detergent and/or sonication for solubilization, PBS-25 is readily soluble in aqueous solutions. This physical property translates to efficient loading of PBS-25 onto CD1d, as measured by isoelectric focusing. Binding of PBS-25 is similar to that of α-GalCer in that the short-chain PBS-25 is bound to CD1 in a way such that the galactose headgroup is located at the boundary between the A' and F' pockets allowing the two alkyl chains to be inserted into each pocket. Both alkyl chains are initially inserted perpendicular to the β-sheet platform and then extend more laterally toward the ends of the A' and F' pockets, respectively. Aromatic residues Tyr73 (A' pocket), Phe77 and Trp133 (F' pocket) make extensive van der Waals interactions with the glycolipid, stabilizing both alkyl chains upon insertion into the individual binding pockets. The 2' and 3' hydroxyl groups of the galactose headgroup of PBS-25 are stabilized by D153 (α2-helix) of CD1d and the 3'-, 4'-hydroxyl groups of the phytosphingosine hydrogen bond to D80. A further "spacer lipid" may also itself into the A' pocket of the CD1d in the cavity normally occupied by a longer alkyl chain; further stabilizing the binding of PBS-25.

The presently disclosed compounds may be compared to one or more of α-GalCer, OCH, or PBS-25 in the examples below, such as by structural analysis, in vitro binding, or in vitro or in vivo activity.

Method of Making

Embodiments herein further provide methods for making the compounds disclosed herein. More particularly, the chemical scheme for making an α-galactoside in good yield with minimal formation of the β-glycoside is shown in Example 1 below (chemical schemes 1 and 2). Further diversification of the α-galactoside and Lewis-acid catalyzed amidation of the α-galactoside provided a diverse group of sphingamides falling within the scope of Formulas I and II.

Composition/Pharmaceutical Formulation

A further embodiment includes a composition including the present sphingamide compounds and one or more other active or inactive ingredients.

Further active ingredients include co-therapies such as spacer lipids or other drugs. Inactive ingredients may include excipients.

"Spacer lipids" include short saturated or unsaturated fatty acyl chains having from four to eighteen carbon atoms.

The term "excipient" as used herein refers to one or more inert substances which are commonly used as a diluent, vehicle, preservative, binder, or stabilizing agent for drugs and includes, but not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). See, also, Remington's Pharmaceutical Sciences (1990) Mack Publishing Co., Easton, Pa., which is hereby incorporated by reference in its entirety.

A further aspect of the composition provides a pharmaceutical formulation comprising the present sphingamide compounds in admixture with a pharmaceutically or veterinarily acceptable adjuvant, diluent or carrier.

Acceptable "carriers" are well known to those of skill in the art and can include, but not be limited to any of the standard pharmaceutical carriers, such as phosphate buffered saline, water and emulsions, such as oil/water emulsions and various types of wetting agents.

Embodiments herein also include compositions comprising pharmaceutically acceptable acid or base addition salts of the sphingamide compounds. The acids which are used to prepare the pharmaceutically acceptable acid addition salts of the aforementioned base compounds are those which form non-toxic acid addition salts, i.e. salts containing pharmacologically acceptable anions, such as the hydrochloride, hydrobromide, hydroiodide, nitrate, sulphate, bisulphate, phosphate, acid phosphate, acetate, lactate, citrate, acid citrate, tartrate, bitartrate, succinate, maieate, fumarate, gluconate, saccarate, benzoate, methanesulphonate, ethanasulphonate, benzenesulphonate, p-toluenesulphonate and parnoate [i.e. 1,1'-methylene-bis-(2-hydroxy-3 naphthoate)] salts, among others.

Pharmaceutically acceptable base addition salts may also be used to produce pharmaceutically acceptable salt forms of the compounds according to embodiments herein.

The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (e.g. potassium and sodium) and alkaline earth metal cations (e.g. calcium and magnesium), ammonium or water-soluble amine addition salts such as N-methylglucamine-(megiumine), and the lower alkanolammonium and other base salts of pharmaceutically acceptable organic amines, among others.

As used herein, 'pharmaceutical formulation' means a therapeutically effective formulation.

A 'therapeutically effective amount', or 'effective amount', or 'therapeutically effective', as used herein, refers to that amount which provides a therapeutic effect for a given condition and administration regimen. This is predetermined quantity of active material calculated to produce a desired therapeutic effect in association with the required additive and diluent, i.e. a carrier or administration vehicle. Further, it is intended to mean an amount sufficient to inhibit, decrease, antagonize, reduce, suppress, or prevent a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions herein, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

More particularly, an "effective amount" or "therapeutically effective amount" of an active agent or therapeutic agent such as the antagonist is an amount sufficient to produce the desired effect, e.g., inhibition of expression of a cytokine in comparison to the normal expression level detected in the absence of the present sphingamide compound, inhibition or decrease of one or more symptoms of an immune modulated disease. Inhibition of expression of a cytokine is achieved when the value obtained is with an antagonist relative to the control is about 95%, 90%, 85%, 80%, 75%, 70%, 65%, 60%, 55%, 50%, 45%, 40%, 35%, 30%, 25%, 20%, 15%, 10%, 5%, or 0% of the value obtained with a control compound. Suitable assays for measuring expression of a target gene or target sequence include, e.g., examination of protein or RNA levels using techniques known to those of skill in the art such as dot blots, northern blots, in situ hybridization, ELISA, immunoprecipitation, enzyme function, as well as phenotypic assays known to those of skill in the art.

It will be appreciated by persons skilled in the art that the sphingamide compounds disclosed herein will generally be administered in admixture with a suitable pharmaceutical excipient, diluent or carrier selected with regard to the intended route of administration and standard pharmaceutical practice (for example, see Remington: The Science and Practice of Pharmacy, 19th edition, 1995, Ed. Alfonso Gennaro, Mack Publishing Company, Pennsylvania, USA). Suitable routes of administration are discussed below, and include topical, intravenous, oral, pulmonary, nasal, aural, ocular, bladder and CNS delivery.

In one embodiment, the pharmaceutical formulation may be a unit dosage containing a daily dose or unit, daily sub-dose or an appropriate fraction thereof, of the active ingredient. Alternatively, the unit dosage may contain a dose (or sub-dose) for delivery at longer intervals, for example bi-weekly, weekly, bi-monthly, monthly, or longer.

The sphingamide compounds and pharmaceutical formulations thereof will normally be administered intranasally, by inhalation, orally, or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the sphingamide compounds may be administered alone but will generally be administered in admixture with a suitable pharmaceutical excipient, diluent or carrier selected with regard to the intended route of administration and standard pharmaceutical practice.

For example, the compounds, i.e. sphingamides, may be administered orally, buccally or sublingually in the form of tablets, capsules, ovules, elixirs, solutions or suspensions, which may contain flavouring or colouring agents, for immediate-, delayed- or controlled-release applications. The compounds herein may also be administered via intracavernosal injection.

Such tablets may contain excipients such as microcrystalline cellulose, lactose, sodium citrate, calcium carbonate, dibasic calcium phosphate and glycine, disintegrants such as starch (corn, potato or tapioca starch), sodium starch glycollate, croscarmellose sodium and certain complex silicates, and granulation binders such as polyvinylpyrrolidone, hydroxypropy-imethylcellulose (HPMC), hydroxy-proplcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Excipients in this regard include lactose, starch, cellulose, milk sugar or high molecular weight polyethylene glycols. For aqueous suspensions and/or elixirs, the compounds herein may be combined with various sweetening or flavoring agents, colouring matter or dyes, with emulsifying and/or suspending agents and with diluents such as water, ethanol, propylene glycol and glycerin, and combinations thereof.

The compounds herein may also be administered parenterally, for example, intravenously, intra-articularly, intra-arterially, intraperitoneally, intra-thecaliy, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (to a pH from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the compounds will usually be from 1 to 1000 mg per adult (i.e. from about 0.015 to 15 mg/kg), administered in single or divided doses. In one aspect, the daily dosage may range from 1 to 750 mg per adult, 1 to 500 mg per adult, or 1 to 250 mg per adult. In another aspect, the daily dosage may be up to 2500 mg per adult. In yet another aspect, the daily dosage may range from 1 to 2500 mg per adult, 100 to 2500 mg per adult, 100 to 1000 mg per adult, 100 to 750 mg per adult, or 100 to 500 mg per adult.

Thus, for example, the tablets or capsules of the compounds herein may contain from 1 mg to 1000 mg of active compound for administration singly or two or more at a time, as appropriate. The physician in any event will determine the actual dosage which will be suitable for any individual patient and it will vary with the age, weight and response of the particular patient. The above dosages are merely exemplary of the average case. There can, of course, be individual instances where higher or lower dosage ranges are merited and such are within the scope of embodiments herein.

The compounds herein may also be administered intranasally or by inhalation and are conveniently delivered in the form of a dry powder inhaler or an aerosol spray presentation from a pressurized container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA 3), carbon dioxide or other suitable gas. In the case of a pressurized aerosol, the dosage unit may be determined by providing a valve to deliver a metered amount. The pressurized container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of compounds disclosed herein and a suitable powder base such as lactose or starch.

Aerosol or dry powder formulations may be arranged so that each metered dose or puff contains at least 1 mg of compounds disclosed herein for delivery to the patient. It will be appreciated that the overall daily dose with an aerosol will vary from patient to patient, and may be administered in a single dose or, more usually, in divided doses throughout the day.

Alternatively, the compounds disclosed herein can be administered in the form of a suppository or pessary, or they may be applied topically in the form of a lotion, solution, cream, ointment or dusting powder. The compounds disclosed herein may also be transdermally administered, for example, by the use of a skin patch. They may also be administered by the ocular route.

For ophthalmic use, the compounds disclosed herein can be formulated as micronised suspensions in isotonic, pH adjusted, sterile saline, or as solutions in isotonic, pH adjusted, sterile saline, optionally in combination with a preservative such as a benzylalkonium chloride. Alternatively, they may be formulated in an ointment such as petrolatum.

For application topically to the skin, the compounds disclosed herein can be formulated as a suitable ointment containing the active compound suspended or dissolved in, for example, a mixture with one or more of the following: mineral oil, liquid petrolatum, white petrolatum, propylene glycol, plyoxethylene polyoxpropylene compound, emulsifying wax and water. Alternatively, they can be formulated as a suitable lotion or cream, suspended or dissolved in, for example, a mixture of one or ore of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Generally, in humans, oral or parenteral administration of the compounds disclosed herein is the most convenient route of administration.

It will be appreciated by persons skilled in the art that such an effective amount of the sphingamide compound or formulation thereof may be delivered as a single bolus dose (i.e. acute administration) or, as a series of doses over time (i.e. chronic administration).

It will be further appreciated by persons skilled in the art that the sphingamide compounds and pharmaceutical formulations thereof have utility in both the medical and veterinary fields. Thus, the methods herein may be used in the treatment of both human and non-human animals (such as horses, dogs and cats). In a particular embodiment, however, the patient is human.

For veterinary use, compounds disclosed herein is administered as a suitably acceptable formulation in accordance with normal veterinary practice and the veterinary surgeon will determine the dosing regimen and route of administration which will be most appropriate for a particular animal.

Thus a further embodiment provides a pharmaceutical formulation comprising an amount of a sphingamide compound effective to inhibit the function of iNKT cell TCR, and a pharmaceutically and biochemically acceptable carrier suitable for parenteral administration in a human.

In further embodiments there are provided sphingamide compounds or a pharmaceutical formulation for use in medicine.

A further aspect of the present sphingamide compounds includes a method of treating an immune modulated disease by administering the sphingamide compound or a pharmaceutical formulation thereof to a patient having the immune modulated disease. As used herein "immune modulated diseases" include: multiple sclerosis, experimental autoimmune encephalomyelitis (both relapsing and remitting), inflammatory conditions (such as rheumatoid arthritis), allergic disorders (such as anaphylactic hypersensitivity, asthma, allergic rhinitis, atopic dermatitis, vernal conjunctivitis, eczema, urticarial, food allergies, allergic encephalomyelitis, multiple sclerosis, insulin-dependent diabetes mellitus, and autoimmune uveoretinitis), inflammatory bowel disease (e.g., Crohn's disease, regional enteritis, distal ileitis, granulomatous enteritis, regional ileitis, terminal ileitis, ulcerative colitis), autoimmune thyroid disease, hypertension, infectious diseases (such as *Leishmania* major, *Mycobacterium leprae, Candida albicans, Toxoplasma gondi*, respiratory syncytial virus, human immunodeficiency virus), allograft rejection (such as graft vs host disease), airway hyper reactivity, atherosclerosis, inflammatory liver disease, and cancer. In a particular aspect, the immune modulated disease may be allograft rejection (such as graft vs host disease), airway hyper reactivity, atherosclerosis, inflammatory liver disease, and cancer.

Embodiments herein provide the use of a sphingamide compound or a pharmaceutical formulation thereof in the preparation of a medicament for treating an immune modulated disease or a disease or condition capable of being treated by an agent which inhibits the function of CD1d or the iNKT cell TCR. Embodiments herein provide sphingamide compounds described herein or a pharmaceutical formulation thereof for treating a disease or condition capable of being treated by an agent which inhibits the function of CD1d or the iNKT cell TCR.

As used herein, and as well-understood in the art, "treatment" is an approach for obtaining beneficial or desired results, including clinical results. In accordance with embodiments herein, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment. Furthermore, the treatment may be prophylactic. The term 'prophylactic' is used to encompass the use of a sphingamide compound or formulation thereof described herein which either prevents or reduces the likelihood of a condition or disease state in a patient or subject.

"Palliating" a disease or disorder means that the extent and/or undesirable clinical manifestations of a disorder or a disease state are lessened and/or time course of the progression is slowed or lengthened, as compared to not treating the disorder. A "delay" in the onset or recurrence of a symptom includes a delay of at least 1 hour, at least 2 hours, at least 6 hours, at least 12 hours, at least 24 hours, at least 48 hours, at least 72 hours, at least 1 week, at least 2 weeks, at least a month, at least three months, at least 6 months, or at least a year. Further, palliation does not necessarily occur by administration of one dose, but often occurs upon administration of a series of doses. Thus, an amount sufficient to palliate a response or disorder may be administered in one or more administrations.

In one embodiment, the present sphingamide compounds prevent one or more symptoms of a condition, or of the generation of an immune response. The term "prevent" as used herein is applied to a patient, in whom symptoms have already been observed at some time in the past or in whom symptoms will develop due to the administration or presence of a triggering agent. By 'treatment' we include both therapeutic and prophylactic treatment of the patient.

To "suppress" or "inhibit" a function or activity, such as cytokine production, antibody production, or histamine release, is to reduce the function or activity when compared to otherwise same conditions except for a condition or parameter of interest, or alternatively, as compared to another condition.

Kits

Kits with unit doses of the subject compounds, usually in oral or injectable doses, are provided. In such kits, in addition to the containers containing the unit doses will be an informational package insert describing the use and attendant benefits of the drugs in treating pathological condition of interest. Exemplary compounds and unit doses are those described herein above.

EXAMPLES

Example 1: Methods of Making Sphingamides

The synthetic pathway towards glycosylacceptor 7 is outlined in scheme 1. The synthesis started from commercially available tri-O-acetyl-D-galactal (1), which is readily converted into 3,4,6-tri-O-benzyl-protected derivative 2. Hydration of the double bond was achieved upon treatment with 4 M sulfuric acid furnishing 2-deoxygalactose intermediate 3. Next, the Wittig reaction of 3 with methyl (triphenylphosphoranylidene)acetate was investigated. Running the reaction in THF results in α,β-unsaturated ester 4 in moderate yield (64%) giving exclusively the E-alkene. When toluene was used as the solvent the reaction yield further increased (79%). Saturation of the double bond was accomplished by conjugate reduction with nickel chloride and sodium borohydride. Mitsunobu reaction with diphenylphosphorazidate (DPPA) converts the C2-OH group of 5 to an azido group (6) and at the same time offers the required stereochemistry. Next the selective deprotection of the primary hydroxyl was achieved by using zinc chloride in acetic anhydride followed by Zemplen deacetylation of the generated acetate to furnish glycosylacceptor 7.

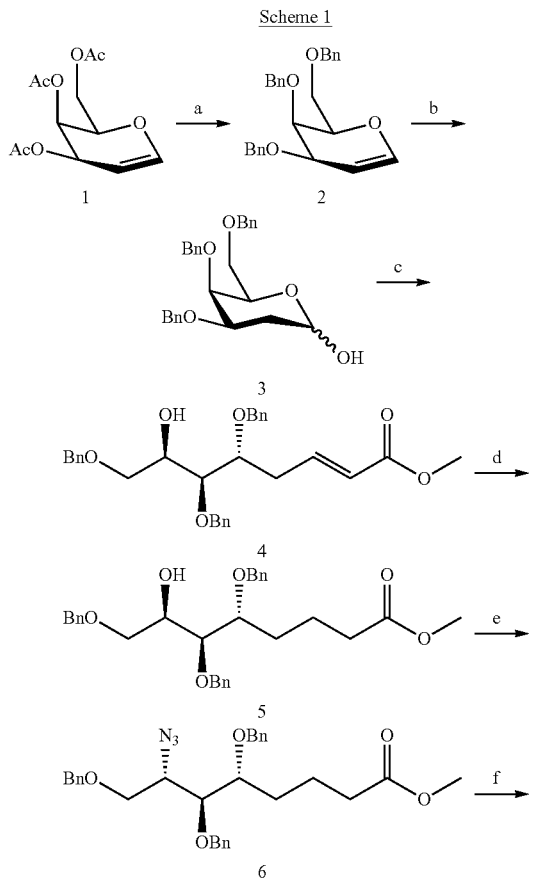

Scheme 1

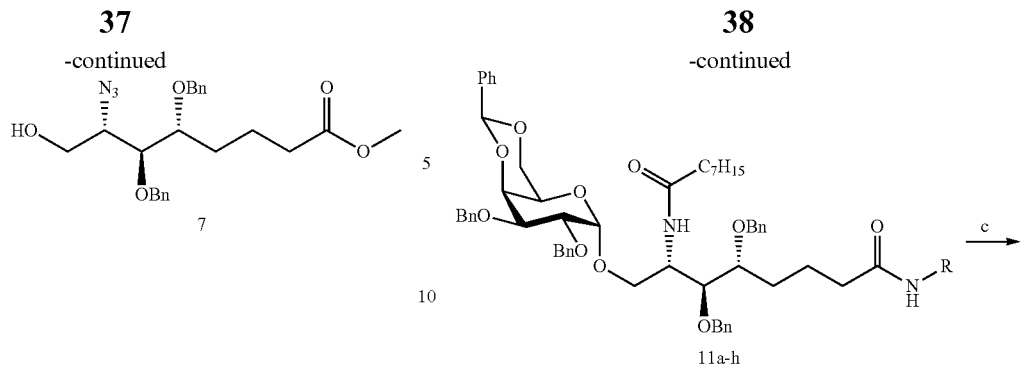

Scheme 2 provides the creation of specific examples of sphingamides described herein. As shown in Scheme 2 below, TMSOTf promoted galactosylation of glycosylacceptor 7 with galactosyl trichloroacetimidate 8 afforded α-galactoside 9 in good yield and without notable formation of the β-glycoside. The ability to diversify the methyl ester after glycosylation is convenient as it reduces the number of linear steps towards the aimed α-GalCer analogues. A Lewis-acid catalyzed amidation with the appropriate amines gave intermediates 10a-h. Next the azido group was subjected to Staudinger reduction with trimethylphosphine and the resulting amines were treated with EDC and octanoic acid to yield 11a-h. Final catalytic hydrogenation afforded the desired derivatives 12a-h.

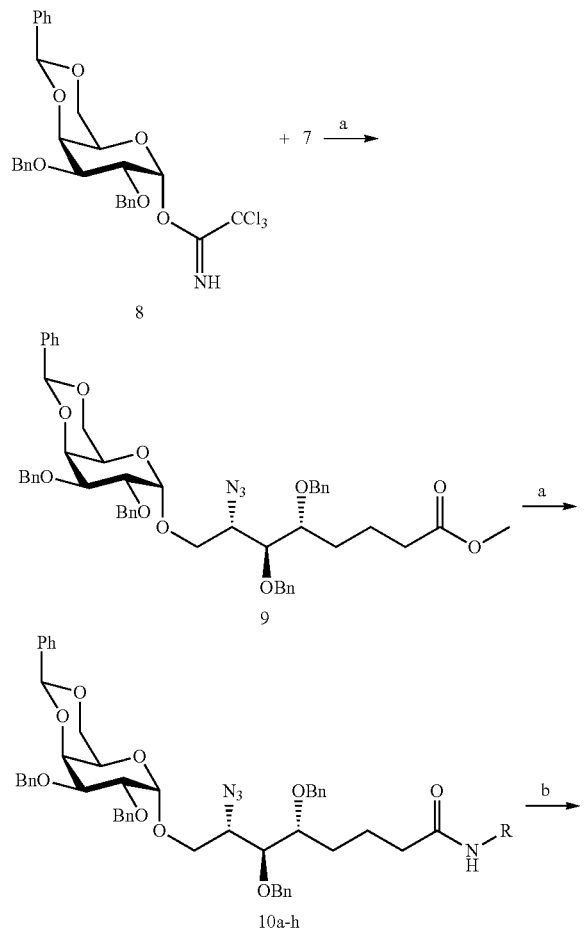

a R = $C_9H_{19}$ (JG081)
b R = $(CH_2)_2Ph$ (JG079)
c R = $(CH_2)_4Ph$ (JG172)
d R = $(CH_2)_6Ph$ (JG168)
e R = $(CH_2)_8Ph$ (JG254)
f R = Ph-m-$C_5H_{11}$ (JG143)
g R = Ph-p-$C_5H_{11}$ (JG076)
h R = $((C_2H_4)_2O)_2C_2H_5$ (JG173)

Example 2: Binding Affinity of Sphingamides with TCR

CD1d was expressed in SF9 insect cells using the baculovirus expression system, biotinylated and loaded with the different sphingamides as reported (PMID 20080535).

SPR studies were conducted using a Biacore T200 (GE Healthcare) as reported previously (Wang et al, 2010). The lipids were loaded to biotinylated birA-tagged mCD1d in the same way as non-birA-tagged mCD1d. In all, 300-500 response units (RU) of mCD1d-glycolipid complexes were immobilized onto a streptavidin sensor chip (Biacore) surface by injection at 5 μl/min (10 mM HEPES, 150 mM NaCl, 3.0 mM EDTA, pH 7.4). A reference surface was generated in another flow channel with unloaded mCD1d immobilized at RU of 500. During the association phase, a series of increasing concentrations of TCR were injected for 3-5 min and the dissociation phase initiated by passage of running buffer alone was continued over 30 min. Experiments were carried out at 25° C. with a flow rate of 30 μl/min and performed at least two to three times, each time with a different batch of TCR preparation. Kinetic parameters were calculated after subtracting the response to mCD1d molecules in the reference channel, using a simple Langmuir 1:1 model in the BIA evaluation software version 4.1. One representative sensorgram for each lipid is shown.

Real-time binding kinetics were calculated by measuring the association-rates ($k_a$) and dissociation rates ($k_d$) of increasing concentrations of soluble TCR to chip-bound CD1d-lipid complexes.

Figure 2:
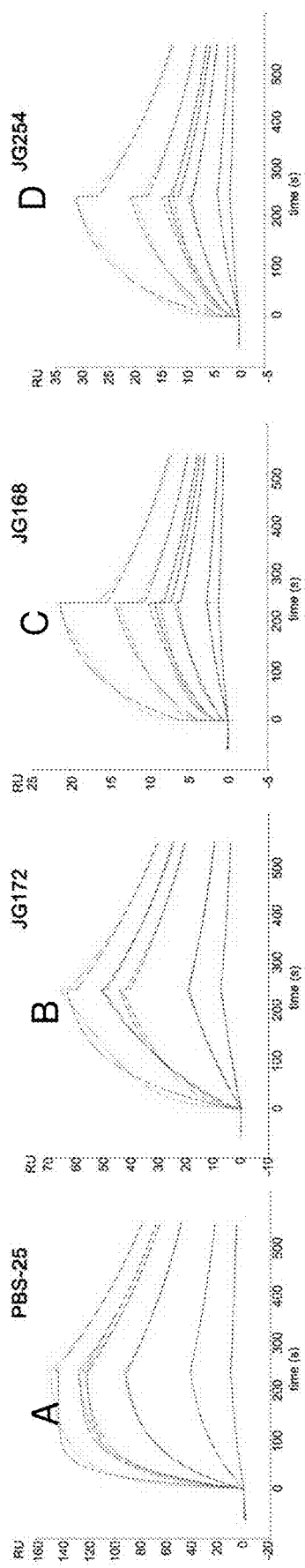
FIG. 2 (A-D) show the binding affinity of reference compound PBS-25 and examples of the present sphingamide compounds in a real-time binding assay called surface plasmon resonance (SPR).

Results are shown in Table 1 below and FIG. 2.

TABLE 1

| Lipid | $k_a$ (1/ms) | $k_d$ (1/s) | $K_D$ (nM) | $chi^2$ | U-value |
|---|---|---|---|---|---|
| PBS 25 | $8.89 * 10^4$ | $2.10 * 10^{-3}$ | 24 | 9 | 1 |
| Jg168 | $8.95 * 10^3$ | $2.20 * 10^{-3}$ | 246 | 0.095 | 1 |
| Jg172 | $2.06 * 10^4$ | $2.26 * 10^{-3}$ | 110 | 1.43 | 1 |
| Jg254 | $9.03 * 10^4$ | $2.45 * 10^{-3}$ | 270 | 0.19 | 1 |

Example 3: Structure of Sphingamide Binding with Cd1d

The crystal structure of sphingamide JG168 bound to mouse CD1d was determined using protein crystallography. Sphingamides were dissolved in DMSO and added to CD1d (in 50 mM Hepes pH7.5, 150 mM NaCl) at a 6:1 molar ratio (sphingamide/CD1d) and incubated o/n at room temperature. Unbound lipid was removed by size exclusion chromatography (SEC) on a Superdex S200 100/300GL column (GE Healthcare) and CD1d-sphingamide complexes were concentrated to 5-10 mg/ml. Crystals were grown at 22.3° C. by sitting drop vapor diffusion by mixing 0.5 µl of CD1d-sphingamide with 0.5 µl of precipitant (20% polyethylene glycol 3350, 8% tacsimate pH 4.0).

Figure 3:
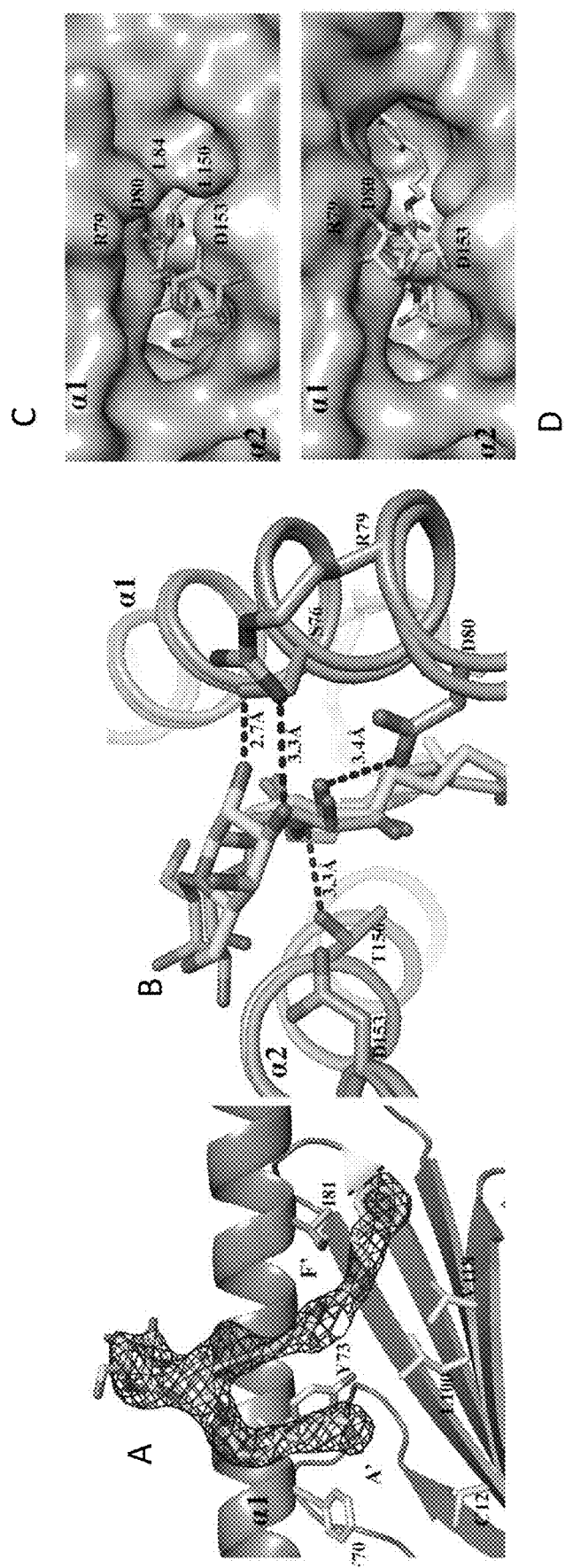
FIG. 3 (A-D) shows the crystal structure of sphingamide JG172 bound to mouse CD1d (A and D) using protein crystallography in comparison to the crystal structure of PBS-25 bound to mouse CD1d (C) with the middle panel (B) being an overlap of JG172 (in yellow) and PBS-25 (in blue). Electron density of JG168 is shown in panel (A) as a blue grid.

Notably, while the iNKT cell TCR can bind the CD1d-JG172 complex with high affinity, as determined by the binding experiments above, the lipid headgroup is presented differently by CD1d compared to the presentation of PBS-25. As shown in FIG. 3B (PBS-25 in blue and JG-172 in yellow). This explains the slightly reduced binding affinity of JG-172 compared to the binding affinity of PBS-25.

Example 4: Structure of Sphingamide Binding with TCR

JG168 sphingamide was loaded onto mCD1d and excess lipid removed as reported above for JG172. The mCD1d-JG168 complex was incubated with TCR (2:1 molar ratio) incubated 30 min on ice and the mCD1d-JG168-TCR complex was purified further by SEC. The ternary complex was concentrated to 3-5 mg/ml in 10 mM Hepes, pH 7.5, 30 mM NaCl. Crystals were grown at 22.3° C. by sitting drop vapor diffusion while by mixing 0.5 µl mCD1d-JG168-mTCR and 0.5 µl precipitate (20% polyethylene glycol 3350, 200 mM magnesium formate).

All crystals were flash-cooled at 100 K in mother liquor containing 25% glycerol. Diffraction data from a single crystal were collected at the Stanford Synchrotron Radiation Laboratory, and were processed with the HKL2000 software to 1.97 Å (mCD1d-JG172), and 2.2 Å (mCD1d-JG168-mTCR) resolution. The mCD1d-JG172 crystal belongs to space group $P2_1$ with cell parameters a=41.58 Å, b=98.22 Å, and c=55.35 Å and β=106.35°. The mCD1d-JG168-mTCR crystal belongs to space group $C222_1$ with cell parameters a=78.18 Å, b=191.17 Å, and c=150.97 Å.

Crystal structures were determined by molecular replacement (MR) using MOLREP as part of the CCP4 suite. The protein mCD1d coordinates from the mCD1d-iGB3 structure (from PDB 2Q7Y) was used for MR of mCD1d-sphingamide and the mouse Vα14Vβ8.2 TCR (from PDB 3QUY) coordinates were used for the mTCR phasing. The REFMAC glycolipid libraries, were created using the Dundee PRODRG2 server (http://davapc1.bioch.dundee.ac.uk/cgi-bin/prodrg). After the MR solutions for both crystal structures were obtained, containing both mCD1d and mTCR, the model was rebuilt into σA-weighted 2Fo–Fc and Fo–Fc difference electron density maps using the program COOT. Structures were refined using iterative cycles of model building in COOT and refinement in REFMACS. The mCD1d-JG172 structure has a final Rcryst=19.7% and Rfree=23.9%, while mCD1d-JG168-mTCR has a final Rcryst=20.6% and Rfree=24.1%. The high quality of both models was confirmed with the program Molprobity.

Upon analysis of the ternary complex of CD1d-JG168-TCR, it was determined that TCR binding induces a structural change in the sphingamides. This structural change moves the headgroup of JG168 back into the conserved position found in PBS-25 (which is also conserved with α-GalCer. As a result, the iNKT cell TCR makes the same conserved interactions with JG168 compared to the other known α-GalCer analogs/derivatives (see FIG. 3).

Figure 4:
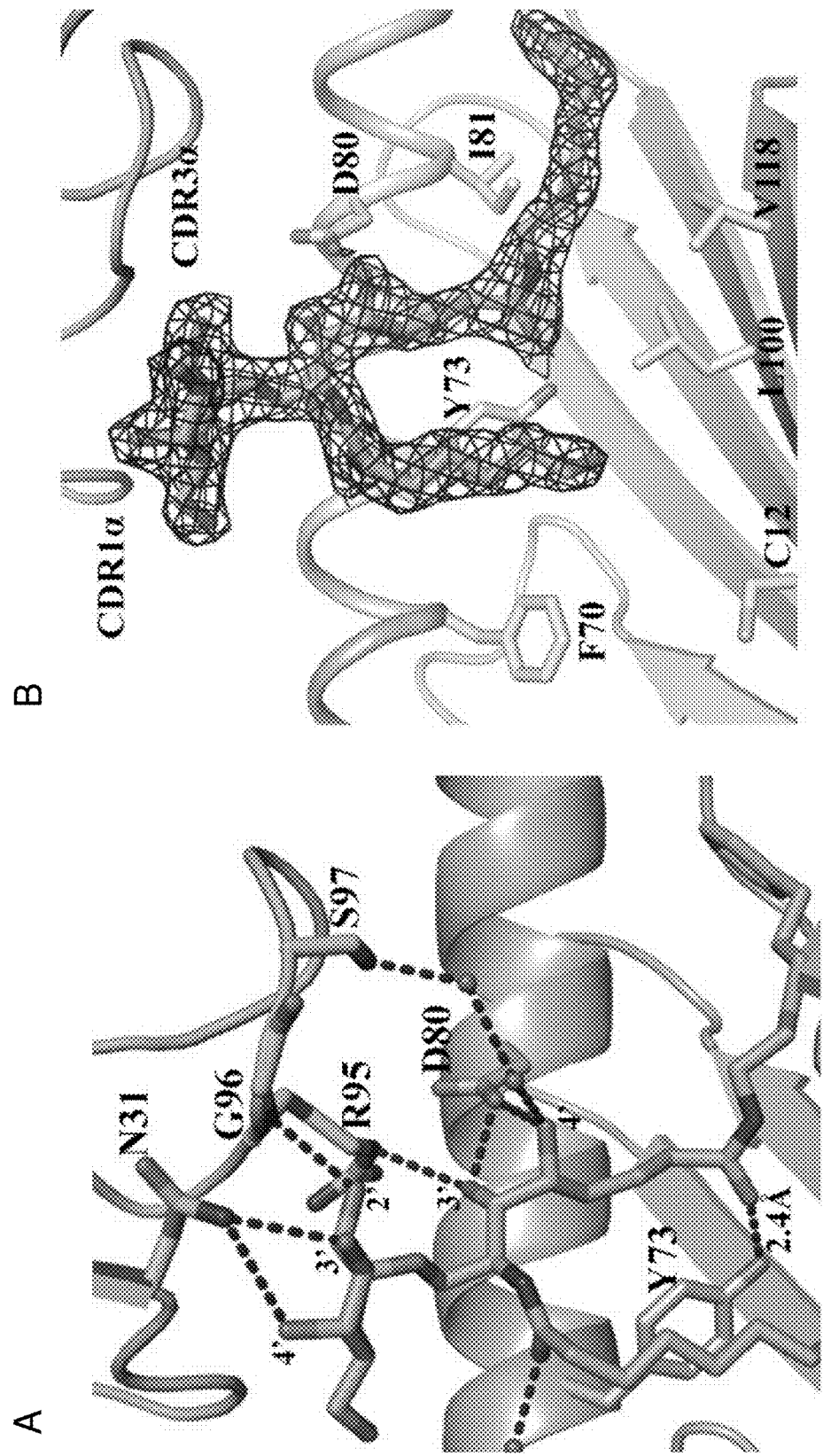
FIG. 4 (A and B) shows the crystal structure of sphingamide JG168 (green) interacting with CD1d (gray) and the mouse iNKT cell TCR (aqua blue) in the ternary complex CD1d-JG-168-TCR, with hydrogen bonds in panel (A) represented as dotted lines and the electron density in panel (B) represented as a blue grid.

Surprisingly, however, the chemical modification with the sphingamide chain (as compared to PBS-25) results in an extra hydrogen-bond between the lipid of the sphingamide and CD1d after TCR binding. This is exemplified with JG172 in particular, which does not form the H-bond in the absence of TCR binding, while in the mCD1d-JG168-mTCR structures this H-bond is formed. As shown in FIG. 4, this hydrogen bond is with the Y73 of the mature mCD1d (SEQ ID NO: 2)(the mouse CD1d without signal sequence or start codon). This additional contact has not been observed for any glycolipid for which crystal structures exist, regardless of whether the complex contained the TCR or not.

Example 5: Activation of iNKT Cells

It was also assessed whether the sphingamides described herein can activate iNKT cell hybridomas using multiple different assays.

a. Activation of Mouse iNKT Cells In Vitro.

First, the present sphingamide compounds were tested to determine whether they activated iNKT cell hybridomas when the sphingamide was presented to the iNKT cell TCR by (a) an antigen presenting-cell (APC) free assay which uses recombinant mCD1d, (b) an A20 B-cell (an antigen presenting cell) expressing the wild-type (WT) mCD1d, or (c) an A20 B-cell expressing a tail-deleted mCD1d. The tail deleted mCD1d lacks the "YQDI" amino acid sorting motif required for routing CD1d to endosomes (for example, amino acid residues 314-317 of SEQ ID NO: 2 would be missing).

For in vitro stimulation, murine iNKT hybridoma cells at $5 \times 10^4$ cells/well in 96-well plates were stimulated with the $10^5$ cells/well glycolipid pulsed BMDCs in cDMEM for 4, 16 or 24 hours at 37° C. with 0.05 µg/ml, 0.1 µg/ml, 0.5 µg/ml, 1 µg/ml, 2 µg/ml, or 5 µg/ml of lipid, and levels of murine IL-2 secretion were determined by ELISA.

Notably, wild type mCD1d can recycle from the cell-surface back into the endosomes/lysosomes, where lipid transfer proteins are present to facilitate exchange of lipids onto CD1d. Tail-deleted mCD1d cannot recycle back into the cell, as the binding site for a required lipid loading factor has been deleted. (see Jin et al., Immunity 2009, 30(6):888-898 for a discussion of the model).

Figure 5:
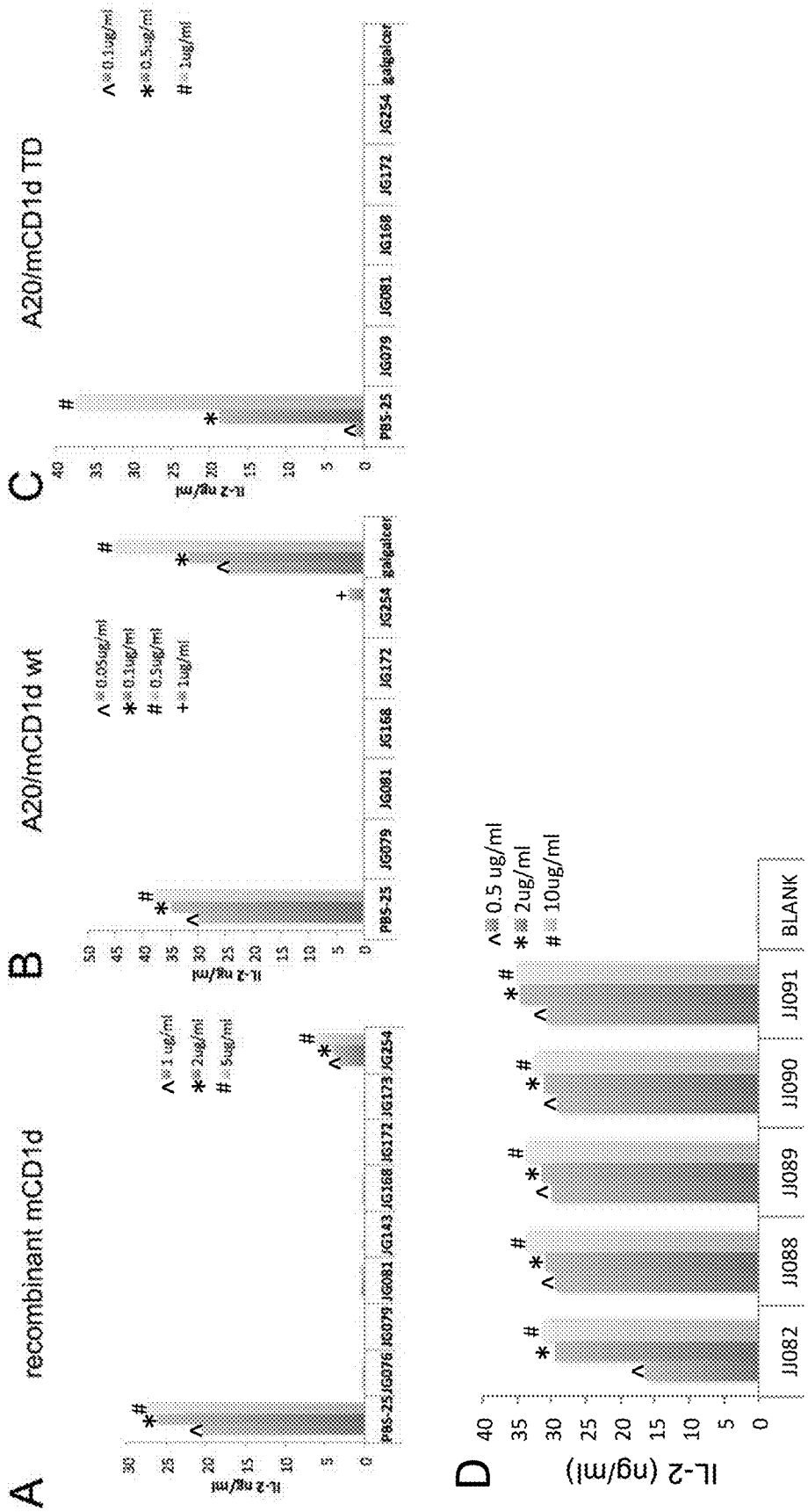
FIG. 5 (A-C) demonstrates that the present sphingamide compounds do not activate iNKT cells in an in vitro assay, whether the sphingamide compound is introduced with a APC-free recombinant mouse CD1d (A), a wild-type mCD1d-transfected A20 B cell (A20/mCD1d wt) (B), or a cytoplasmic tail deletion mutant mCD1d-transfected A20 B cell (C), which lacks the "YQDI" amino add sorting motif required for routing CD1d to endosomes.

As shown in FIG. 5 (A-C), PBS-25 activated iNKT cells producing a significant amount of IL-2 using each of the CD1d models (see FIG. 5A-C). Notably, PBS-25 is known for particularly efficient lipid loading onto CD1d due to the shorter lipid chain length (See Zajonc 2005 Nat. Immunol. 6(8):810-818). In contrast, the sphingamide compounds described herein did not stimulate the secretion of significant amounts of IL-2 in any of the models (FIG. 5A-C). α-Gal-Cer stimulated the secretion of IL-2 in the wild-type, APC bound CD1d model, but did not stimulate IL-2 production in the tail-deleted CD1d model, as the α-GalCer loading was prevented by the truncation of the CD1d protein (compare FIGS. 5B and C). FIG. 5D is a control experiment, identical to panel FIG. 5A but using lipids that lack the amide group, which makes them all agonists as expected. This Example demonstrates that the amide group prevents iNKT cell activation.

b. Activation of Mouse iNKT Cells In Vivo.

For in vivo activation of iNKT cells C57BL/6 mice were intravenously injected with 5 µg glycolipid dissolved in DMSO and diluted with vehicle (50 mM Tris-HCl pH 7.0, 4.8 mg/ml sucrose, 0.5 mg/ml sodium deoxycholate, and 0.022% Tween 20)

Cytokine levels were measured from blood serum using ELISA after 4 hours (IL-4) and 16 hours (IFN-γ).

Figure 6:
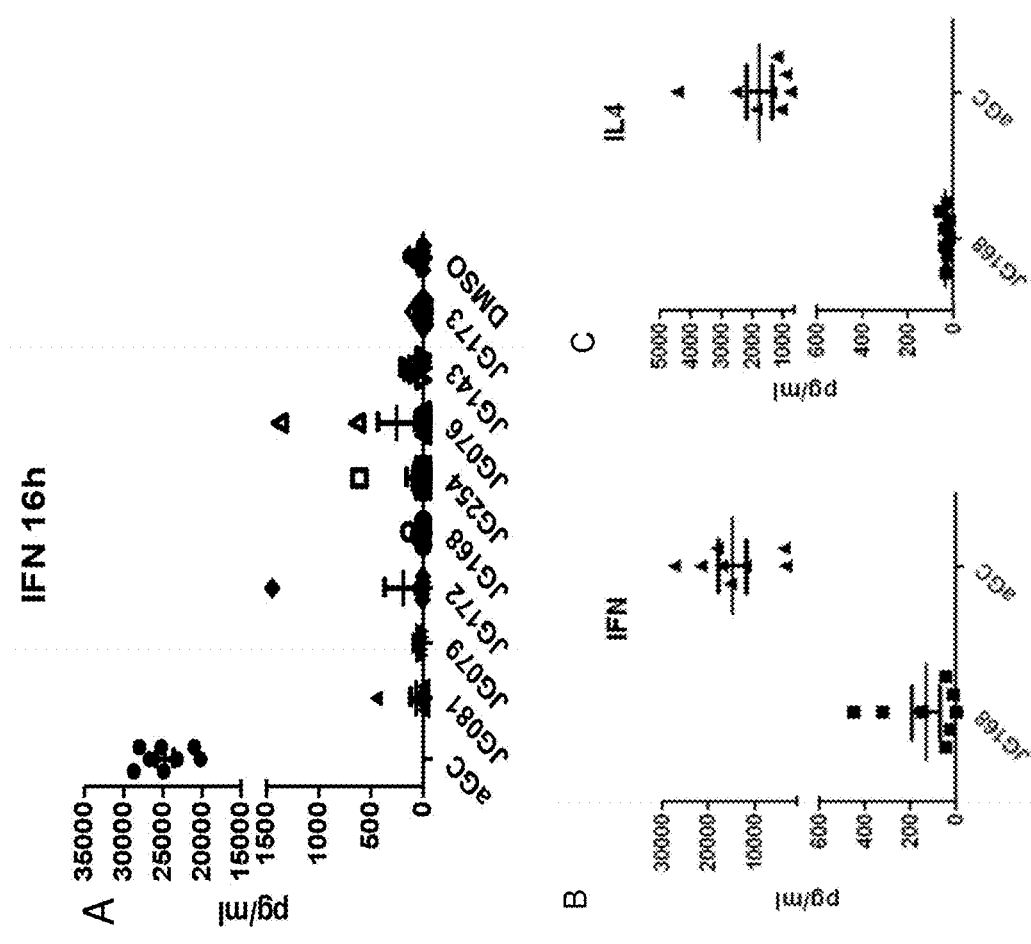
FIG. 6 (A-C) shows that the present sphingamide compounds do not activate iNKT cells in vivo with either the production of IFN-γ or IL-4.

Results are shown in FIG. 6 (A-C). As expected, α-Gal-Cer produced significant amounts of IFN-γ and IL-4. The sphingamide compounds did not produce significant levels of either IFN-γ or IL-4.

c. Activation of Human iNKT Cells In Vitro.

The isolation and expansion of human Vα24$^+$ NKT cell lines has been published previously (Rogers, P. R., Matsumoto, A., Naidenko, O., Kronenberg, M., Mikayama, T., and Kato, S. (2004) Expansion of human Vα24$^+$ NKT cells by repeated stimulation with KRN7000. J. Immunol. Methods 285, 197-214). Human donor peripheral blood mononuclear cells (PBMCs, 1-1.5×10$^6$/ml) were isolated and cultured in RPMI 1640 medium (Invitrogen) supplemented with 10% (v/v) FBS and 1% (v/v) Pen/Strep/glutamine (10,000 units of penicillin, 10 mg of streptomycin, 29.2 mg/ml L-glutamine; Invitrogen), and cultures were expanded by weekly re-stimulation with αGalCer-pulsed, irradiated PBMC and recombinant human IL-2.

PBMCs (1×10$^5$ per well) were pulsed with glycolipids, seeded in 96-well plates, and cultured in the presence of 5×10$^4$ Vα24$^+$ human NKT cells for 24 h. GM-CSF release was evaluated in a sandwich ELISA following the manufacturer's instructions (R&D Systems).

Notably, as GM-CSF is found in high levels in joints with rheumatoid arthritis, blocking GM-CSF production may reduce the inflammation or damage caused by the disease.

Figure 7:
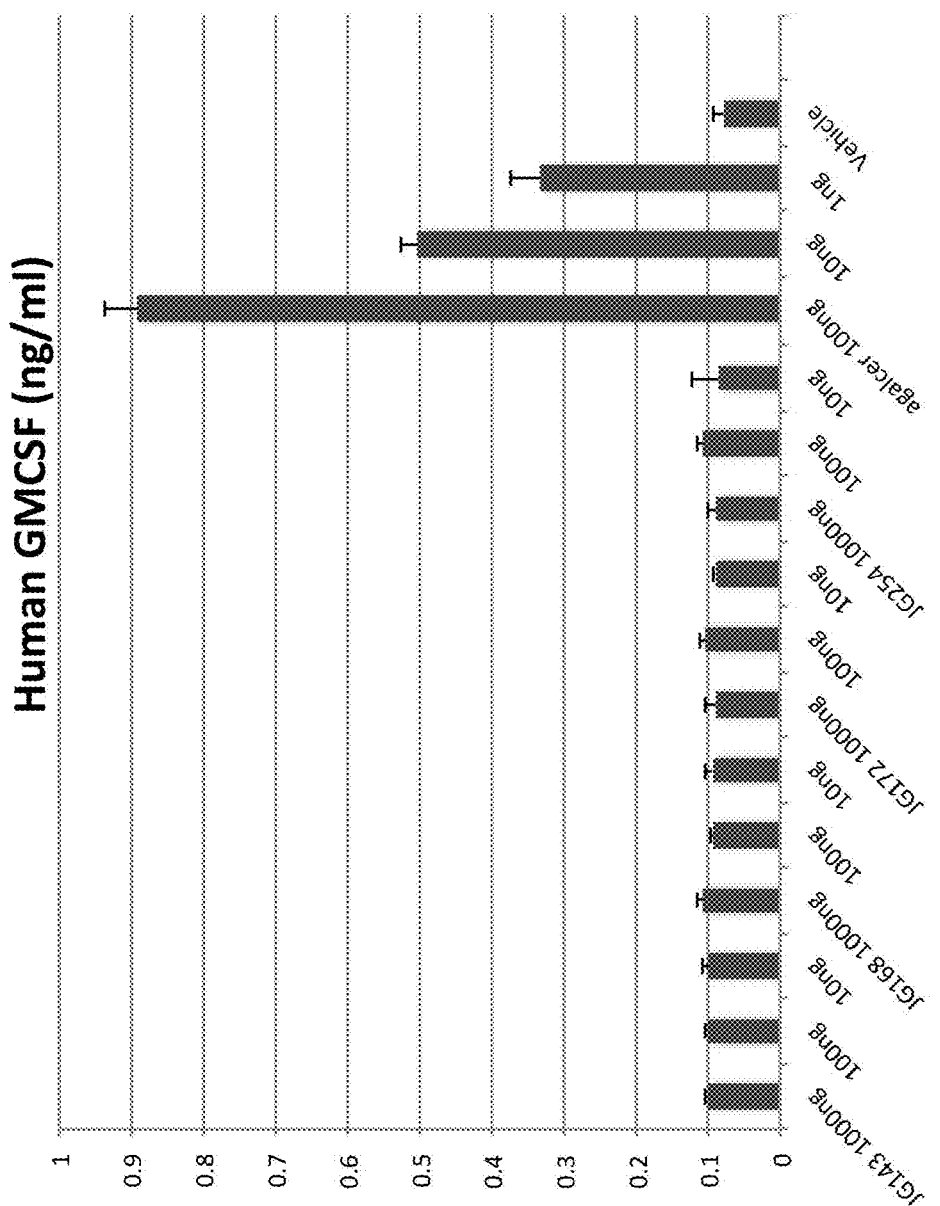
FIG. 7 shows that the present sphingamide compounds do not activate human iNKT cells based on human GMCSF production.

As shown in FIG. 7, the presently described sphingamide compounds did not cause the secretion of GMCSF. In contrast, α-GalCer caused significant secretion of GMCSF at all doses.

Example 6: Sphingamide Competition with OCH In Vitro

The antigen presenting-cell (APC) free system using recombinant mCD1d was used to demonstrate whether the present compositions compete with OCH for APC binding. Increasing concentrations of JG168 (1-20 ug/ml) was mixed with 100 ng (1 ug/ml final conc) OCH and incubated with recombinant mCD1d.

For in vitro stimulation, murine iNKT hybridoma cells at 5×10$^4$ cells/well in 96-well plates were incubated with CD1d (loaded with OCH and the competing sphingamide) and levels of iNKT cell activation was monitored by measuring murine IL-2 secretion by ELISA.

Figure 8:
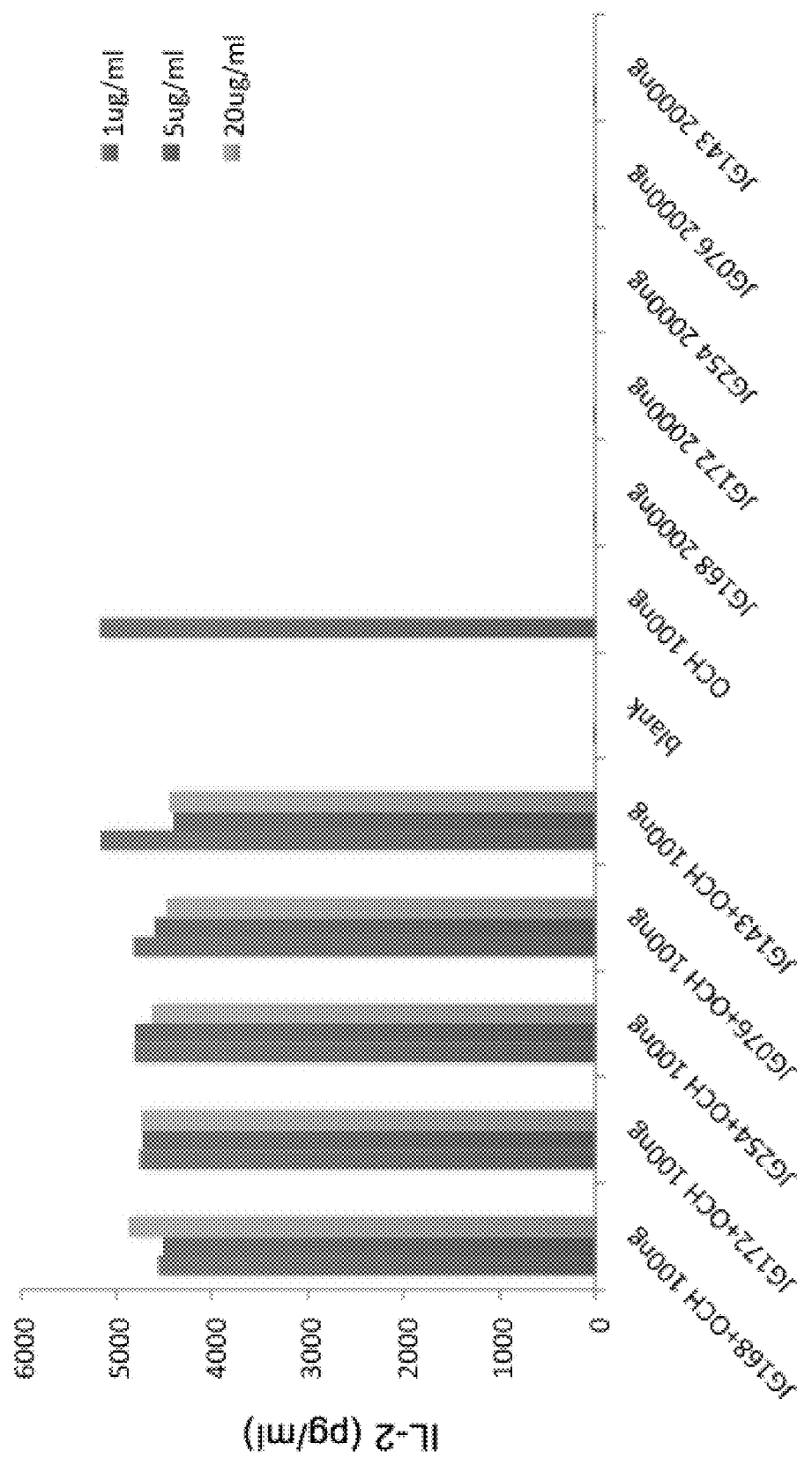
FIG. 8 shows that the present sphingamide compounds do not compete with OCH in vitro.

No competition was observed. It is hypothesized that OCH binds mCD1d with higher affinity than the sphingamides since it has a longer (C24 vs. C8) acyl chain, and therefore, OCH occupied all binding sites of CD1d. See FIG. 8.

Example 7: Sphingamide Competition with OCH In Vivo

For in vivo activation of iNKT cells C57BL/6 mice were intravenously injected with 1 µg JG168+1 µg OCH, 5 µg JG168+1 µg OCH, 20 µg JG168+1 µg OCH, DMSO+1 µg OCH, DMSO, 20 µg JG168 alone or 1 or 2 µg OCH alone. Cytokine levels were measured from blood serum using ELISA after 4 hours (IL-4) and 16 hours (IFN-γ).

Figure 9:
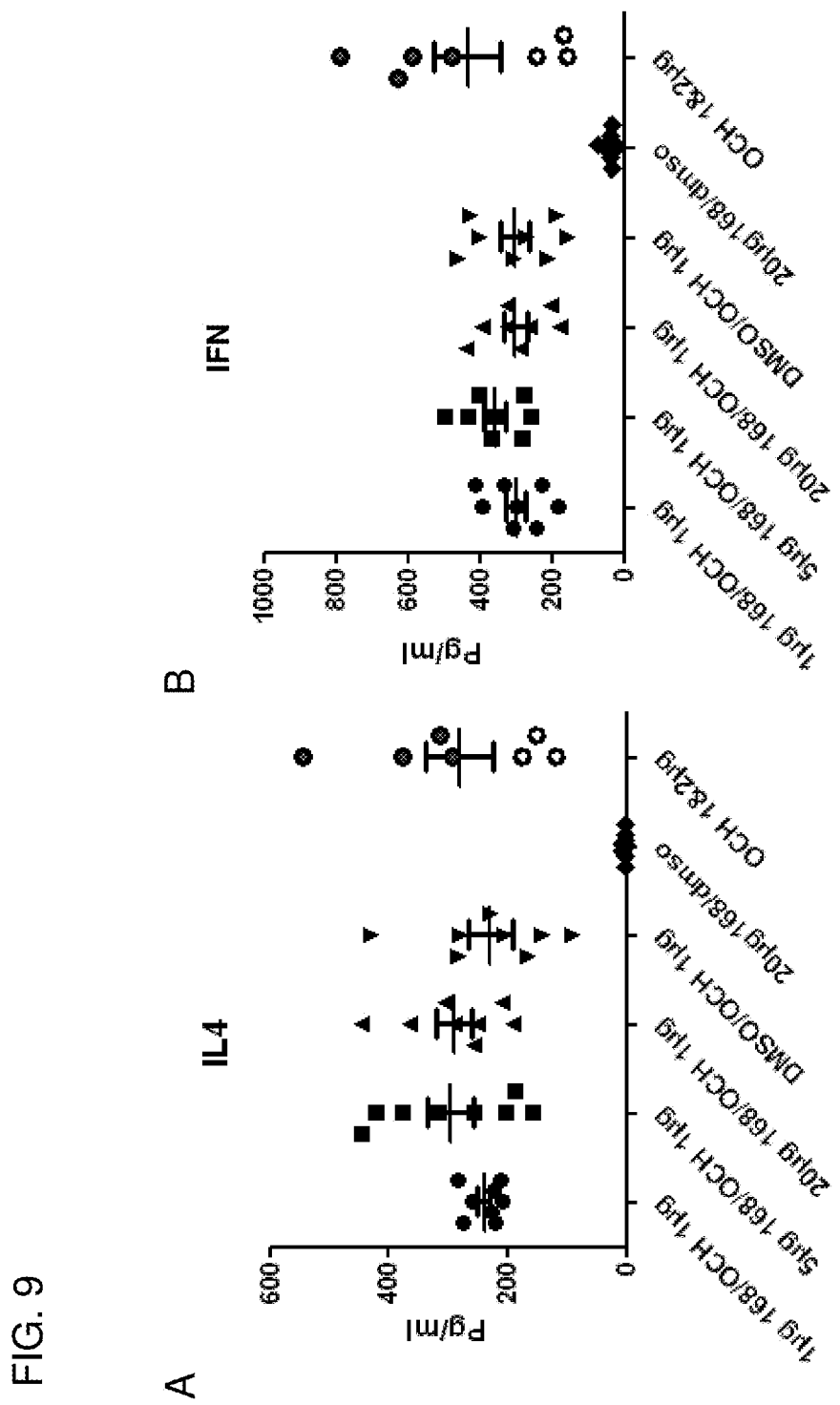
FIG. 9 shows that sphingamide compounds do not compete with longer lipids, such as OCH in vivo, as shown by the consistent production of IL-4 and IFN-γ.
Figure 10:
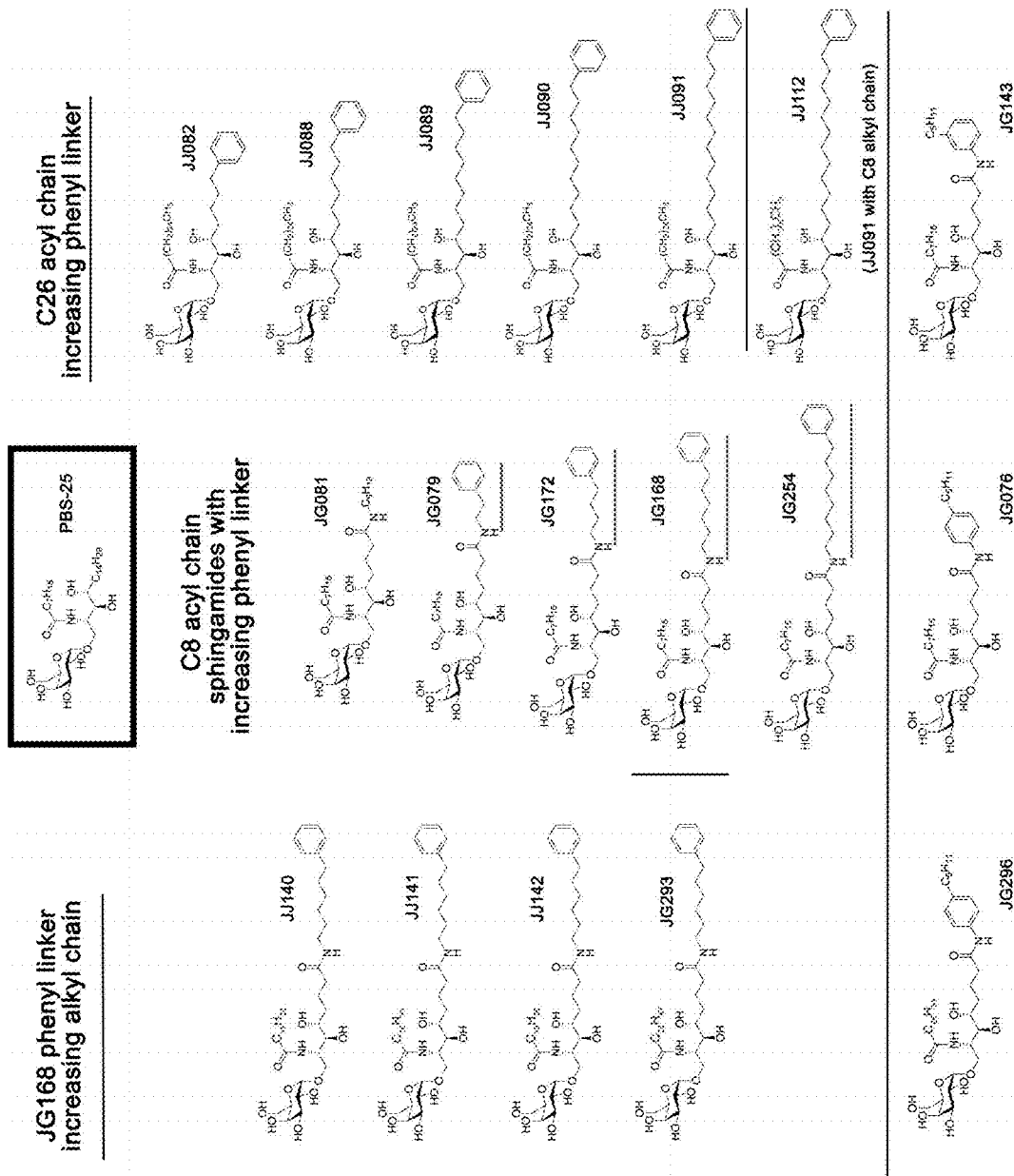
FIG. 10 shows exemplary compounds in accordance with embodiments herein.

Again, no competition was observed, and as expected JG168 did not activate iNKT cells in vivo, see FIG. 9.

Example 8: Induction of AHR and Measurement of Airway after Treatment with Sphingamide AHR responses are assessed by methacholine-induced airflow obstruction in conscious mice placed in a whole-body plethysmograph (Buxco Electronics, Troy, N.Y.) (see Lombardi et al., J. Immunol. 2010, 184(4):2107-2115). In some experiments, AHR is assessed by invasive measurement of airway resistance, in which anesthetized and tracheostomized mice were mechanically ventilated using a modified version of a method described earlier. Aerosolized methacholine is administered for 20 breaths in increasing concentrations (1.25, 2.5, 5, and 10 mg/ml of methacholine). Lung resistance (LR) and dynamic compliance (Cdyn) are continuously computed by fitting flow, volume, and pressure to an equation of motion.

Mice challenged intranasally with α-GalCer develop severe AHR within 24 hours. Other lipids and self-antigens may also have this effect. To determine whether the present sphingamide compound inhibit or prevent the development of AHR, a single dose is administered prior to the induction of AHR by α-GalCer or another compound. To induce α-GalCer-dependent AHR, α-GalCer is administered intranasally (1 µg α-GalCer in 50 µl PBS) to mice anesthetized with ketamine and xylazine. 24 hours later AHR is measured by PenH in a whole-body plethysmograph.

Figure 11:
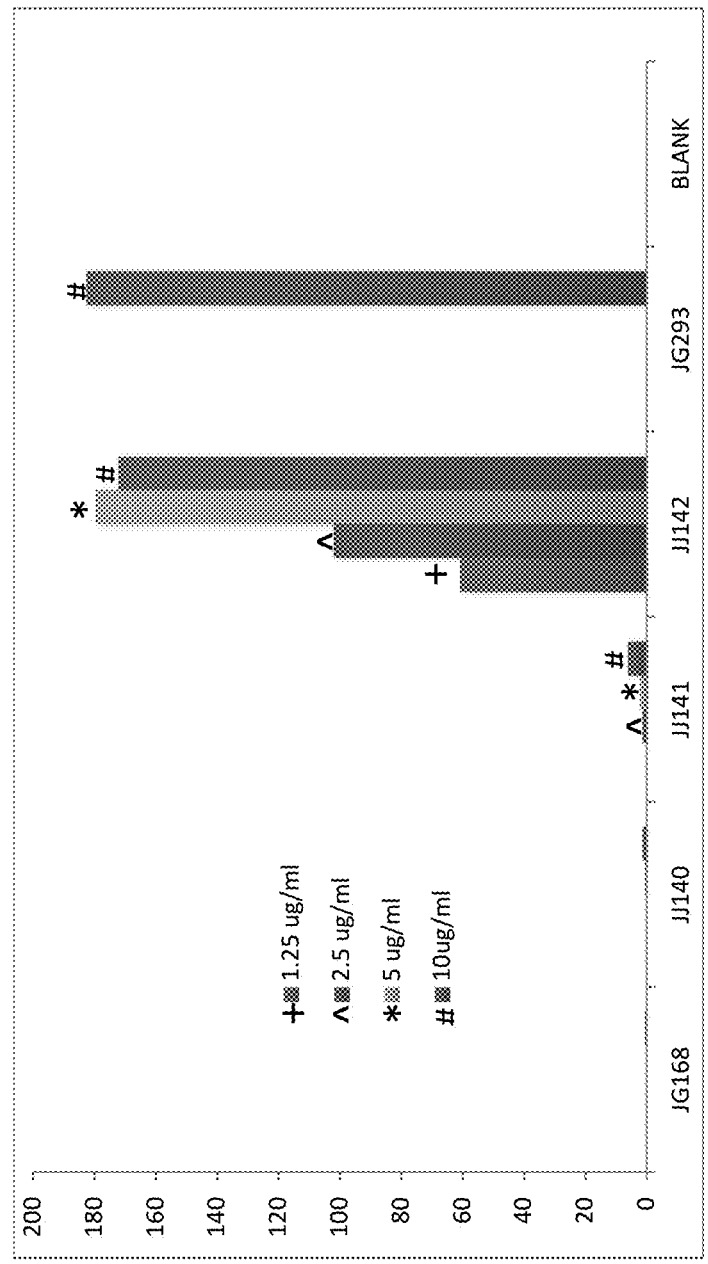
FIG. 11 shows a bar graph of sphingamide, or amide-lacking versions thereof tested to determine if they activated iNKT cell hybridomas when the sphingamide was presented to the iNKT cell TCR by an antigen presenting-cell (APC) free assay.

Example 9: FIG. 11 Shows Results Under Experimental Conditions Identical to FIG. 5A The present sphingamide, or amide-lacking versions were tested to determine whether they activated iNKT cell hybridomas when the sphingamide was presented to the iNKT cell TCR by an antigen presenting-cell (APC) free assay which uses recombinant mCD1d. 1 µg mouse CD1d was coated on 96-well plates and washed and loaded with indicated amounts of sphingamides (125 ng, 250 ng, 500 ng and 1000 ng per well) over night at room temperature. Excess lipids was removed and plates were blocked with 1% BSA in PBS.

For in vitro stimulation, murine iNKT hybridoma cells at 5×10$^4$ cells/well were added to the wells containing CD1d and incubated in the presence of 5% CO2 at 37° C. over night. Levels of murine IL-2 secretion were determined by ELISA.

Figure 12:
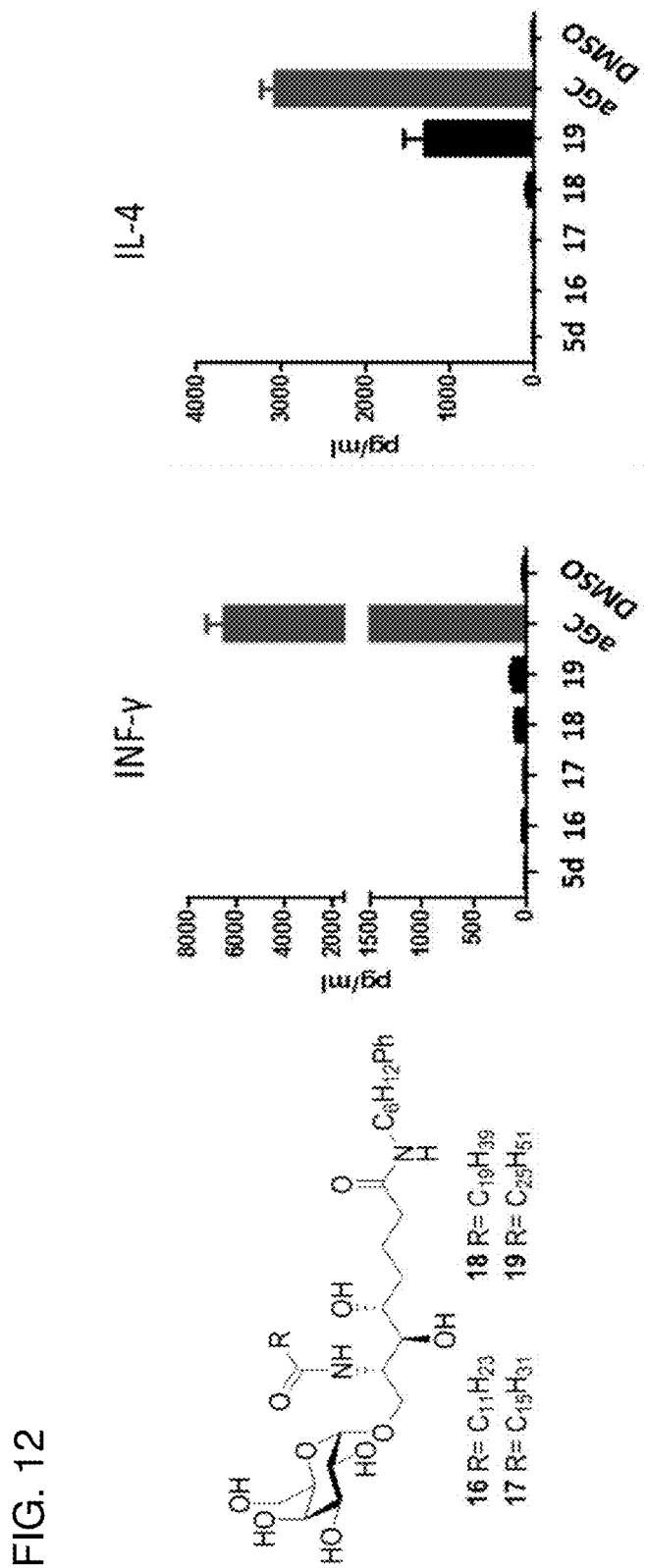
FIG. 12 shows an in vivo study (1 ug glycolipid injected i.v.) as performed as for the other in vivo studies herein.

FIG. 12 shows an in vivo study (1 µg glycolipid injected i.v.) and performed as for the other in vivo studies herein.

The longer the chain the better the sphingamide will compete with αGalCer for CD1d binding and the more potent it will block activation of iNKT cells. The Example investigates at what chain length the sphingamides become anti-activating. Because the JG293 sphingamide showed activation in vitro intermediate chain length versions were synthesized.

In vitro data: increasing acyl chain length to 20 and 26 carbons (methylene units) restores iNKT cells activation. JJ141 emerges as a favorable candidate for competition studies. Although the reason for activation is currently unknown, it is believed that the acyl chain affects overall presentation of the sphingamide to the iNKT cell.

In vivo data: Only long chain JG293 is weakly active (while JJ142 is also active in vitro) and this activity only leads to IL-4 production. As a result, JG293 is a TH-2 biasing glycolipid (similar to OCH) and can also be used to reduce TH1-driven inflammatory conditions. (Rather than inhibiting the inflammatory IfN-g production by iNKT cells, we can activate iNKT cells to only make the counter-acting TH2 cytokine IL4. aGalCer as a control makes both which traditionally hampers its therapeutic potential.

Figure 13:
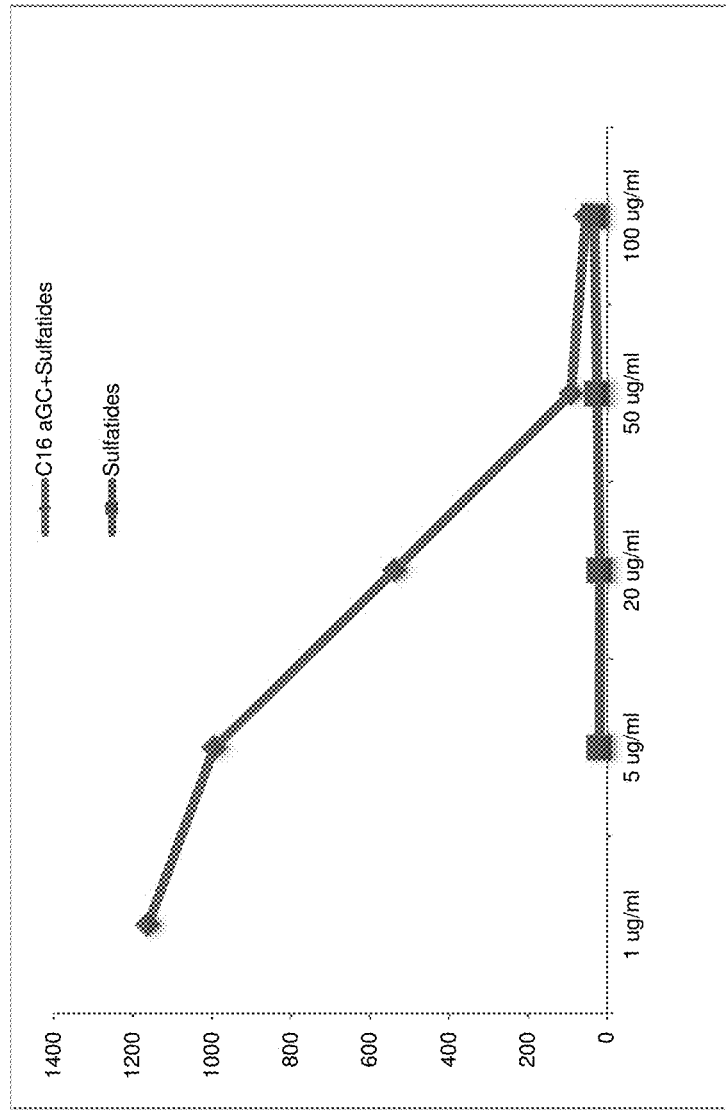
FIG. 13 shows a plot of the inhibition of Hy1.2 activation by sulfatide.

FIG. 13. shows inhibition of Hy1.2 activation by sulfatide. 0.75 μg/ml C16-aGalCer was mixed with indicated concentration and added to CD1d coated plates o/n at RT. Displacement of aGalCer by bovine brain sulfatides led to reduced activation (IL-2 release in pg) of the iNKT cell hybridoma. Sulfatides by itself (squares) did not activate the iNKT hybridoma.

This provides proof that glycolipids (here sulfatide) can compete with aGalCer and reduce iNKT cell activation. Here a fixed concentration of the activating lipid aGalCer (750 ng/well) is used and loaded into CD1d together with increasing concentrations of sulfatide (0.5 ug, 2 ug, 5 ug and 10 ug/well).

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present embodiments, which is defined solely by the claims. Accordingly, the present embodiments are not limited to that precisely as shown and described.

Of course, variations on these described embodiments will become apparent to those of ordinary skill in the art upon reading the foregoing description. Accordingly, embodiments herein include all modifications and equivalents of the subject matter recited in the claims appended hereto as permitted by applicable law. Moreover, any combination of the above-described embodiments in all possible variations thereof is encompassed by this disclosure unless otherwise indicated herein or otherwise clearly contradicted by context.

Groupings of alternative embodiments, elements, or steps are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the embodiments are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present embodiments (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present embodiments and does not pose a limitation on the scope of the embodiments otherwise claimed. No language in the present specification should be construed as indicating any non-claimed element essential to the practice of the embodiments herein.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the various embodiments. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed:

1. A compound of formula I, or a pharmaceutically acceptable salt thereof:

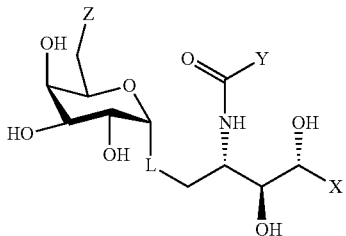

Formula I wherein X represents an alkyl chain having 3 to 30 carbons and having:
  i. at least one intervening amide group and terminating in a phenyl group; or
  ii. a terminating alkyl substituted anilide;
wherein Y is an alkyl chain having 5 to 30 carbons;
wherein Z represents OH;
wherein L represents an oxygen atom or a C-glycoside analogue thereof.

2. The compound according to claim 1 having the structure of formula II, or a pharmaceutically acceptable salt thereof:

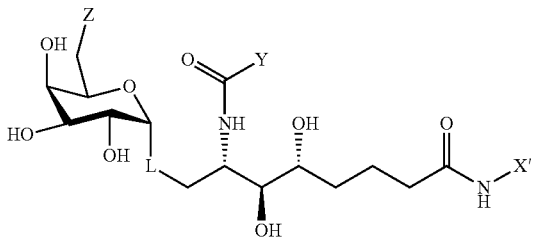

Formula II wherein X' is:
  i. an alkyl chain having two to 8 carbons terminating in a phenyl group; or
  ii. an alkyl substituted phenyl group.

3. The compound according to claim 2, wherein X' is selected from the group consisting of:

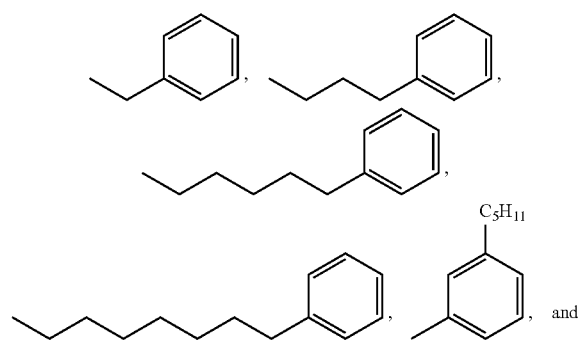

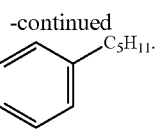

4. The compound according to claim 1, wherein Y is selected from the group consisting of:
  a $C_{27}H_{55}$ unbranched alkyl chain;
  a $C_{25}H_{51}$ unbranched alkyl chain;
  a $C_{23}H_{47}$ unbranched alkyl chain; and
  a $C_7H_{15}$ unbranched alkyl chain.

5. The compound of claim 1, wherein the compound binds one or more of CD1 or an NKT cell TCR.

6. The compound according to claim 5, wherein the CD1 is CD1d and the NKT cell TCR is an iNKT cell TCR.

7. The compound according to claim 6, wherein the CD1d id a human CD1d sequence having the amino acid sequence of SEQ ID NO: 4 or a sequence having substantial identity thereto.

8. The compound according to claim 6 wherein the compound binds CD1d in a non-conserved manner when compared to the binding of α-GalCer.

9. The compound according to claim 6, wherein the compound binds an iNKT cell TCR in a conserved manner when compared to the binding of α-GalCer.

10. The compound according to claim 6, wherein the binding affinity to CD1d or the iNKT cell TCR is in the nanomolar range.

11. A composition comprising the compound of claim 1 and one or more additional active ingredients and/or one or more inactive ingredients.

12. The composition according to claim 11, wherein the active ingredient is a spacer lipid.

13. The compound according to claim 1, having the structure of:

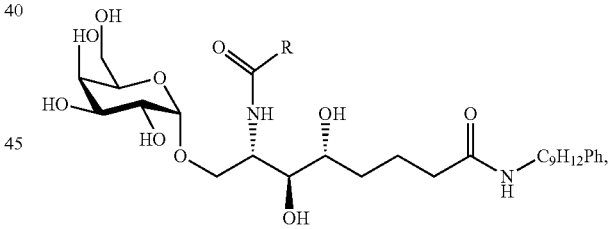

wherein $R=C_{25}H_{51}$.

14. The compound according to claim 1, having the structure of:

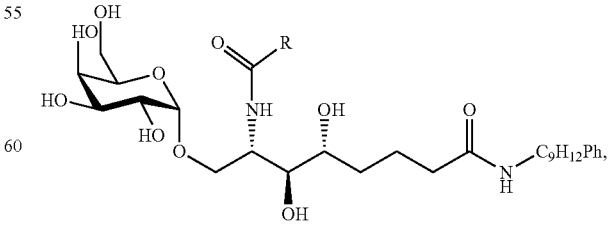

wherein $R=C_{19}H_{39}$.

15. The compound according to claim 1, having the structure of:

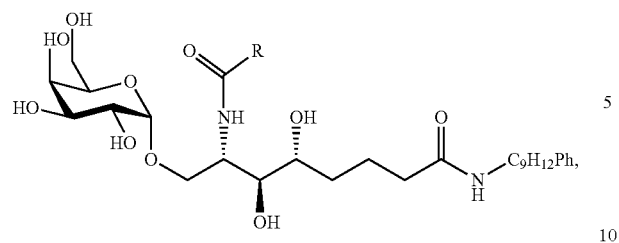
wherein R=$C_{15}H_{31}$.
16. The compound according to claim 1, having the structure of:
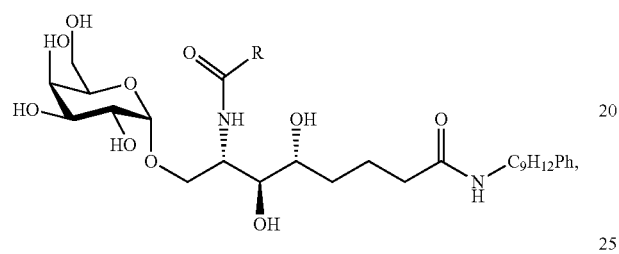
wherein R=$C_{11}H_{23}$.
* * * * *